(12) United States Patent
Yue et al.

(10) Patent No.: US 9,709,557 B2
(45) Date of Patent: Jul. 18, 2017

(54) ANTHRAQUINONE BASED NEAR IR EMITTING COMPOUNDS AND USES THEREOF

(71) Applicant: LIFE TECHNOLOGIES CORPORATION, Carlsbad, CA (US)

(72) Inventors: Stephen Yue, Eugene, OR (US); Shih-Jung Huang, Eugene, OR (US); Jolene Bradford, Eugene, OR (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 14/632,168

(22) Filed: Feb. 26, 2015

(65) Prior Publication Data

US 2015/0168383 A1 Jun. 18, 2015

Related U.S. Application Data

(62) Division of application No. 13/126,234, filed as application No. PCT/US2009/061392 on Oct. 20, 2009, now Pat. No. 8,999,965.

(60) Provisional application No. 61/108,721, filed on Oct. 27, 2008.

(51) Int. Cl.
| | |
|---|---|
| *G01N 33/52* | (2006.01) |
| *C12Q 1/68* | (2006.01) |
| *C09B 1/516* | (2006.01) |
| *C07H 21/04* | (2006.01) |
| *G01N 21/64* | (2006.01) |

(52) U.S. Cl.
CPC ............. *G01N 33/52* (2013.01); *C07H 21/04* (2013.01); *C09B 1/5165* (2013.01); *C12Q 1/6816* (2013.01); *C12Q 1/6841* (2013.01); *G01N 21/6428* (2013.01); *G01N 2021/6441* (2013.01)

(58) Field of Classification Search
CPC ........... C07C 50/18; C07C 50/20; C12Q 1/68; C12Q 1/6816; C12Q 1/6841
See application file for complete search history.

(56) References Cited

U.S. PATENT DOCUMENTS

| | | |
|---|---|---|
| 3,236,864 A | 2/1966 | Blout et al. |
| 3,418,342 A | 12/1968 | Buecheler et al. |
| 5,132,327 A | 7/1992 | Patterson |
| 6,468,753 B1 | 10/2002 | Smith et al. |
| 7,060,427 B2 | 6/2006 | Smith et al. |
| 2003/0130272 A1 | 7/2003 | Mincher et al. |
| 2006/0148777 A1 | 7/2006 | Smith et al. |
| 2008/0168608 A1 | 7/2008 | Plos et al. |

FOREIGN PATENT DOCUMENTS

| | | |
|---|---|---|
| EP | 0044026 | 1/1982 |
| EP | 01086178 | 9/2003 |
| EP | 1905801 | 4/2008 |
| EP | 2362890 | 9/2011 |
| JP | 60172591 | 9/1985 |
| JP | 61041382 | 2/1986 |
| JP | 10195328 | 7/1998 |
| WO | WO-91/05824 | 5/1991 |
| WO | WO-96/34916 | 11/1996 |
| WO | WO-99/65992 | 12/1999 |
| WO | WO-2006/089809 | 8/2006 |
| WO | WO-2008/037394 | 4/2008 |
| WO | WO-2009/063020 | 5/2009 |
| WO | WO-2010028349 | 3/2010 |
| WO | WO-2010/062499 | 6/2010 |
| WO | WO-2010/062499 A3 | 7/2010 |

OTHER PUBLICATIONS

Chemical Abstract, , "RN 95219-21-9", 1985.
Chemical Abstracts, , "RN", 41450-23-1, 1984.
EP 09829545.4, , "Extended European Search Report mailed", Sep. 20, 2012.
PCT/US09/61392, , "International Preliminary Report on Patentability Mailed May 12, 2011", 8.
PCT/US2009/061392, , "International Preliminary Report on Patentability mailed", May 12, 2011.
PCT/US2009/061392, , "International Search Report and Written Opinion Mailed May 19, 2010", 13.

*Primary Examiner* — Craig Ricci
*Assistant Examiner* — Christopher R Stone

(57) ABSTRACT

Disclosed are near IR emitting fluorescent compounds; methods of making and kits containing the described compounds; and their use in fluorescence-based detection of biological materials.

6 Claims, 6 Drawing Sheets

ANTHRAQUINONE BASED NEAR IR EMITTING COMPOUNDS AND USES THEREOF

CROSS-REFERENCE TO RELATED APPLICATIONS

This application is a divisional application of U.S. application Ser. No. 13/126,234, filed Oct. 18, 2011, which is a U.S. National Stage Application of PCT application no. PCT/US09/61392, filed Oct. 20, 2009, which claims priority to U.S. application No. 61/108,721, filed Oct. 27, 2008, which disclosures are herein incorporated by reference in their entirety.

FIELD OF THE INVENTION

The present application relates to anthraquinone-based near IR emitting compounds; kits containing the described compounds; and their use in fluorescence-based detection of biological materials.

BACKGROUND OF THE INVENTION

Fluorescent compounds can be used to directly stain or label a sample so that the sample can be identified and quantitated. Fluorescent dyes are widely used in biological applications in which a highly sensitive detection reagent is desirable. For example, fluorescent dyes may be added as part of an assay for a biological target analyte. Dyes that are able to preferentially bind to a specific biological component in a sample can be used to determine the presence or quantity of that specific ingredient. Exemplary uses of biological staining include detection of cells or bare nuclei with flow cytometry and in vivo and in vitro imaging applications.

Fluorescent dyes with longer wavelength absorption and emission are particularly useful in conjunction with materials of biological origin such as cells and tissues, where background or inherent fluorescence or absorption often interferes with detection of the added fluorescent dye. Furthermore, biological specimens often have decreasing levels of both absorption and fluorescence emission as the illumination energy approaches the infrared.

Biological stains are often membrane permeant and stain both live and dead cells. Depending on the application, staining of live cells may be preferable. For example, live cell staining can provide information about the rate of cell cycling in a population of cells. Staining of live cells can be achieved using a combination of an organelle or membrane stain and a cell permeant nucleic acid stain.

There exists a need for fluorescent compounds that selectively stain live cells and have emission spectra in the near IR region.

SUMMARY OF THE INVENTION

Anthraquinone-based near IR emitting compounds and methods for their preparation; kits containing the described compounds; and their use in fluorescence-based detection of biological materials are provided.

The compounds of the invention may be used in standard fluorescence-based assays (e.g., live and dead cell staining) and with equipment known to those skilled in the art. The subject dyes are relatively stable to photobleaching, remaining intensely fluorescent even after repeated exposure to the intense illumination. The subject compounds can penetrate cell membranes of dead and living cells. In particular, the subject compounds can penetrate the cellular membrane and the nuclear membrane without the addition of fixatives and/or permeabilizing reagents, which can cause excessive variability in the results. Penetration of living cell membranes by the subject dyes can allow for staining of nucleic acids within the cell, making these compounds particularly useful for nucleus labeling and in the detection of DNA content in living cells. Live stain staining also allows for the possibility of sorting of cells populations based on DNA content and then growing the sorted cells for further testing. The subject compounds exhibit minimal cytotoxicity, making them particularly useful in applications involving live cells. The subject compounds emit in the near IR region of the spectrum after irradiation at an appropriate wavelength of light. Due to their optical properties, the subject compounds can be used for staining and detection of biological materials (e.g., cells, bare nuclei, and tissues) and in multiplexing applications in combination with other fluorescent or non-fluorescent probes (e.g., fluorochrome-labeled antibodies).

In one aspect, the present invention provides compounds having the structure:

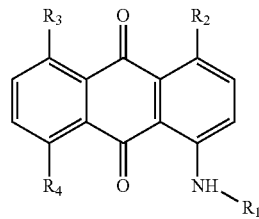

or a salt thereof, wherein $R_2$, $R_3$, and $R_4$ are independently OH or $NHR_9$, and wherein at least one of $R_2$, $R_3$, and $R_4$ is OH, and wherein $R_1$ and $R_9$ independently comprise 1-30 atoms selected from the group consisting of N, O, C, H, and combinations thereof.

In another aspect, the present invention provides compounds having a structure:

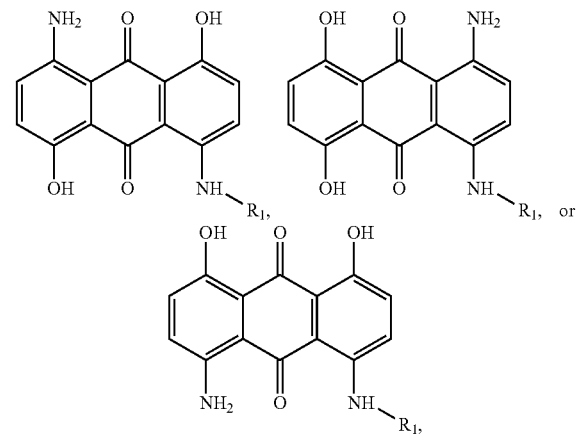

or a salt thereof, where substituent $R_1$ is as described above.

In yet another aspect, a compound is provided having the structure:

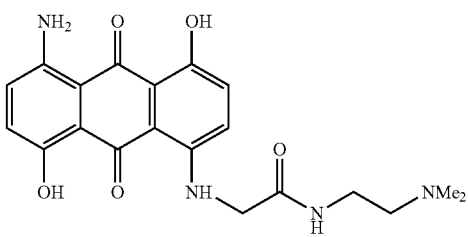 [SMILES: CN(C)CCNC(=O)CNc1ccc(O)c2c1C(=O)c1c(O)ccc(N)c1C2=O]

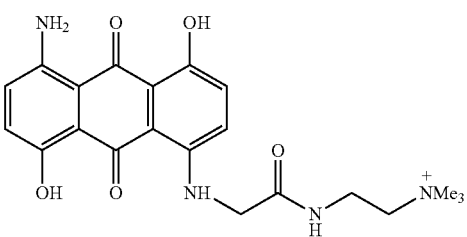

or a salt thereof.

In another aspect, a complex of a nucleic acid molecule (e.g., DNA) and an anthraquinone-based compound of the invention is provided.

The present invention further provides methods of preparing and using the described compounds. For example, methods for detecting the presence of (and optionally quantitating) nucleic acids in a sample are provided.

In one aspect, a method is provided for detecting the presence of a nucleic acid in a sample, comprising:
combining a compound, as described herein, with a sample to form a mixture;
incubating the mixture for a sufficient amount of time for the compound to associate with nucleic acid in the sample;
illuminating the incubated sample with an appropriate wavelength to generate a detectable optical response; and detecting the optical response of the compound.

In yet another aspect, the present invention provides compounds having the structure:

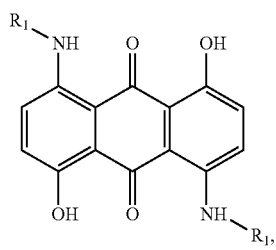

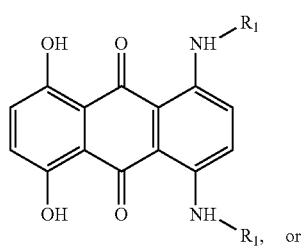

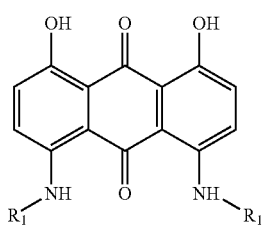

or a salt thereof, where substituent $R_1$ is as described above.

In yet another aspect, a compound is provided having the structure:

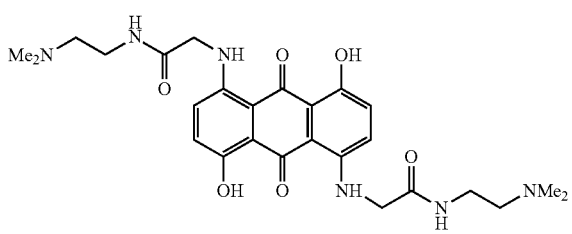 [SMILES: CN(C)CCNC(=O)CNc1ccc(O)c2c1C(=O)c1c(O)ccc(NCC(=O)NCCN(C)C)c1C2=O]

In yet another aspect, a compound is provided having the structure:

In yet another aspect, a method of staining a biological sample containing nucleic acid is provided. The method includes contacting the biological sample with a compound, as described herein.

In yet another aspect, a method of quantifying nucleic acid content in live cells is provided, comprising:
combining a compound, as described herein, with a sample to form a mixture, wherein the sample comprises a nucleic acid molecule;
incubating the mixture for a sufficient amount of time for the compound to associate with the nucleic acid in the sample;
illuminating the incubated sample with an appropriate wavelength to generate a detectable optical response; and
detecting the presence of nucleic acid in the sample by flow cytometric analysis, image cytometry analysis, image analysis including, or high content image analysis.

In yet another aspect, a method is provided for detecting the presence of live cells in a sample, comprising:
combining a compound, as described herein, with a sample to form a mixture;
incubating the mixture for a sufficient amount of time for the compound to associate with a nucleic acid in the sample;
illuminating the incubated sample with an appropriate wavelength to generate a detectable optical response; and
detecting the presence of the nucleic acid by imaging.

In yet another aspect, a method is provided for detecting the presence of fixed cells in a sample, comprising:
combining a compound, as described herein, with a sample to form a mixture, wherein the sample comprises fixed cells, wherein the cells comprise a nucleic acid molecule;
incubating the mixture for a sufficient amount of time for the compound to associate with the nucleic acid molecule in the sample;
illuminating the incubated sample with an appropriate wavelength to generate a detectable optical response; and
detecting the presence of the nucleic acid molecule.

The method of any one of claims 37-61 wherein 5 μM or more of the compound is combined with the sample.

In yet another aspect, the present invention provides kits that include the described compounds. For example, a kit is provided for detecting nucleic acids in a sample, wherein the kit comprises:
- a compound, as described herein; and
- one or more components selected from a sample preparation reagent, a buffering agent, an organic solvent, and components for testing of other cell functions in conjunction with the compound.

DETAILED DESCRIPTION OF THE INVENTION

Figure 1:
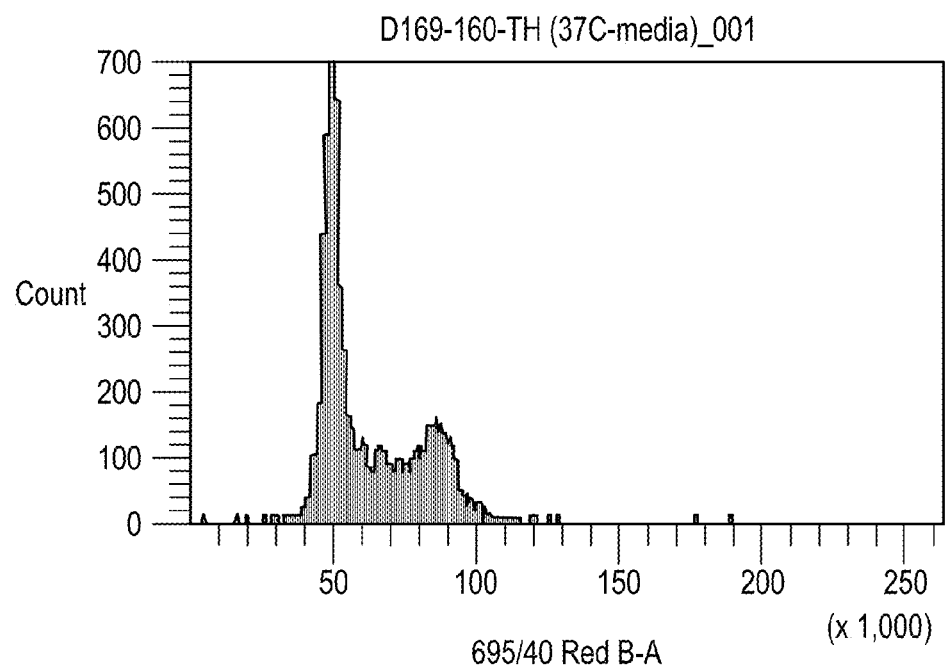
FIG. 1 shows a cell cycle histogram for live Jurkat cells suspended in RPMI media+10% FBS treated with 5 uM Compound 9 and incubated for 30 minutes at 37° C., acquisition using 633 nm excitation and 695/40BP emission.

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. It also should be noted that the term "about", when used to describe a numerical value, shall encompass a range up to ±15% of that numerical value, unless the context clearly dictates otherwise.

Unless defined otherwise, all technical and scientific terms used herein have the same meaning as commonly understood by one of ordinary skill in the art to which this invention is related. The following terms are defined for purposes of the invention as described herein: "Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" refers to an alkyl chain.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The term "dye" as used herein refers to a compound that emits light to produce an observable detectable signal.

The present invention provides anthraquinone-based fluorescent compounds that absorb light having a wavelength of about 450-700 nm and emit in the near IR region of the electromagnetic spectrum. The anthraquinone-based compounds provided herein can be represented by the chemical structure of Formula 1:

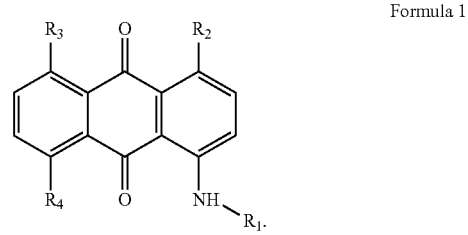

Formula 1

The substituents $R_2$, $R_3$, and $R_4$ are independently OH or $NHR_9$, at least one of substituents $R_2$, $R_3$, and $R_4$ is OH; and substituents $R_1$ and $R_9$ independently form a moiety that contains 1-30 atoms, where the atoms may be N, O, C, H, or any combination thereof. $R_1$ and $R_9$ may independently include a linear, branched or cyclic moiety. The moiety may include an aliphatic group and/or an aromatic group. In certain embodiments, $R_1$ is formed from a combination of C, H, O, and N atoms. In certain embodiments, $R_1$ includes an amide moiety (—CONH—)

Selected examples of the anthraquinone-based compounds of Formula 1 include a substituent $R_9$ that is a moiety containing one hydrogen atom. Selected examples of anthraquinone-based compounds in which $R_9$ is H can be represented by the chemical structures of Formula 2-4:

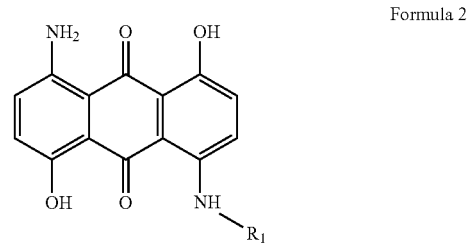

Formula 2

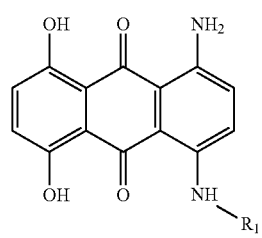

Formula 3

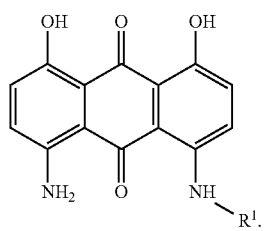

Formula 4

Selected examples of the anthraquinone-based compounds provided herein can include a substituent $R_1$ having a structure —$(CH_2)_nCOR_5$. The number of —$CH_2$— groups (n) in $R_1$ may vary from 1 to 5. In certain embodiments, n is 1 or 2. $R_5$ is a moiety formed of 1-30 atoms selected from N, O, C, H, and combinations thereof. In certain embodiments, $R_5$ is formed from a combination of C, O, N, and H atoms. In certain embodiments, $R_5$ includes an amide moiety. For example $R_5$ can be $N(R_6)$-A-$NR_7R_8$, wherein $R_6$, $R_7$, $R_8$, and A independently are H or a moiety formed from 1-30 atoms selected from N, O, C, H, and combinations thereof. $R_6$, $R_7$, $R_8$, and A can include a moiety which is linear, branched, or cyclic and can include an aromatic and/or aliphatic moiety. In other embodiments, $R_1$ can be H, $C_{1-10}$ alkyl, $C_{1-10}$ hydroxyalkyl, or $C_{1-10}$ aminoalkyl. In yet other embodiments, $R_6$ is hydrogen. Moiety A can include an alkylene group having 2-10 carbons (e.g., $(CH_2)_{2-10}$). In certain embodiments, $R_7$ and $R_8$ independently include 1-10 carbon atoms. $R_7$ and/or $R_8$ can be a $C_{1-10}$ alkyl group, such as methyl, ethyl, and the like. For certain compounds, $R_7$ and $R_8$ are the same alkyl group (e.g., methyl). Selected compounds include a substituent $R_5$ that is $NH(CH_2)_mNR_7R_8$, wherein $R_7$ and $R_8$ are independently H or $C_{1-10}$ alkyls; m is 2-10; and n is 1 to 5.

One selected example of an anthraquinone-based compound described herein can be represented by the chemical structure of Formula 5:

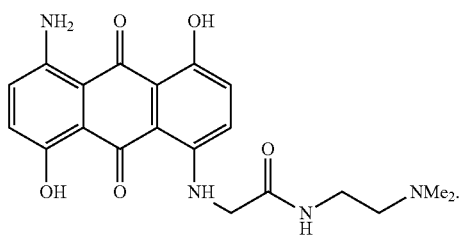

Formula 5

Another example of an anthraquinone-based compound provided herein includes a substituent $R_2$, $R_3$, or $R_4$ where at least one of substituents $R_2$, $R_3$, or $R_4$ has a structure NH—$R_1$, where $R_1$ has been described above. Selected examples of such compounds may be represented by the chemical structures of Formula 6-8:

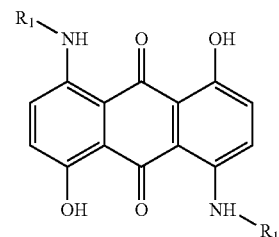

Formula 6

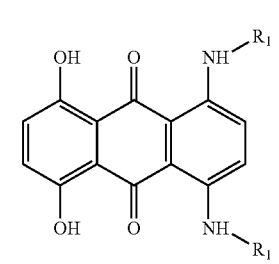

Formula 7

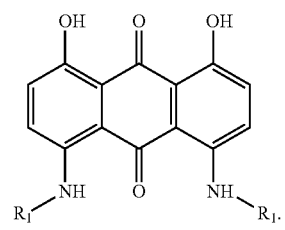

Formula 8

In certain embodiments, $R_1$ is formed from a combination of C, O, N, and H atoms. In certain embodiments, $R_1$ includes an amide moiety. Representative examples of compounds having a structure represented by Formulas 6-8 include a substituent $R_1$ which is —$CH_2COR_5$, wherein $R_5$ is a moiety formed of 1-30 atoms selected from the group consisting of N, O, C, H, and combinations thereof. In certain embodiments, $R_5$ is formed from a combination of C, O, N, and H atoms. In certain embodiments, $R_5$ includes an amide moiety. In certain embodiments, $R_5$ can be $N(R_6)$-A-$NR_7R_8$, wherein $R_6$, $R_7$, $R_8$, and A independently are H or a moiety formed from 1-30 atoms selected from N, O, C, and combinations thereof. $R_6$, $R_7$, $R_8$, and A can include a moiety which is linear, branched, or cyclic and which can include an aromatic and/or aliphatic moiety. A can include an alkylene group having 2-10 carbons (e.g., $(CH_2)_{2-10}$). In certain embodiments, $R_7$ and $R_8$ independently include 2-10 carbon atoms, such as an alkyl group (e.g., methyl, ethyl, and the like). For certain compounds, $R_7$ and $R_8$ are the same alkyl group (e.g., methyl).

One selected example of an anthraquinone-based compound described herein can be represented by the chemical structure of Formula 9:

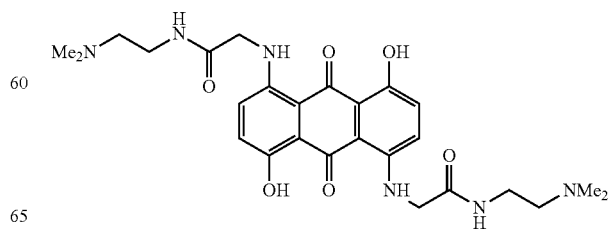

Formula 9

Certain compounds include a moiety $R_5$ that includes a quarternized nitrogen atom. Compounds containing quarternized nitrogen atoms may have certain advantages when used as dead cell stains, in particular.

The compounds of the present invention may be prepared in the form of a salt. For example, the salt may be a compound having a quarternized nitrogen atom. The salt may include a counterion, such as, for example, Cl—, Br—, I—, $ClO_4$—OAc—, $SO_4$—, tartrate, or citrate. Salts of the compounds described herein may be prepared using methods (e.g., counterion exchange using column chromatography techniques) that are well known to those skilled in the art, and representative methods for preparation of salts are further described in the examples below.

In one embodiment, the salt may include a compound having a chemical structure represented by Formula 1, wherein $R_1$ is —$(CH_2)_nCOR_5$, where n is 1 to 5. $R_5$ is as described herein. In some embodiments, $R_5$ may be formed from a combination of C, O, N, and H atoms. In some embodiments, $R_5$ includes an amide moiety. For example, $R_5$ may be $NH(CH_2)_nN(+)R_{10}R_{11}R_{12}$, wherein $R_{10}$, $R_{11}$, and $R_{12}$ are independently H or $C_{1-10}$ alkyl. In one embodiment of the invention, $R_1$ is —$(CH_2)_nCOR_5$, where X is O; $R_5$ is $NH(CH_2)_mN(+)R_{10}R_{11}R_{12}$, wherein $R_{10}$, $R_{11}$, and $R_{12}$ independently are H or $C_{1-10}$ alkyl, m is 2-10; and n is 1 to 5.

An exemplary salt may include a compound having a chemical structure represented by Formula 10.

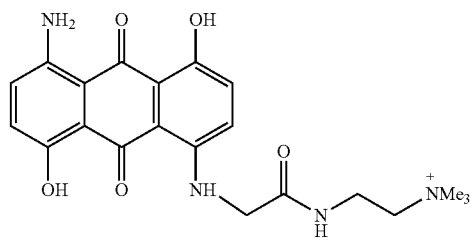

Formula 10

The compound of Formula 10 may further include a counterion. For example, the compound of Formula 10 may be prepared as an iodide salt. Alternative derivatives may be prepared by derivatizing a compound according to Formula 10 with HCl or acetic acid.

The compounds of the invention are soluble in biologically compatible solvents, such as water, buffer, media, media with additions like serum or antibiotics, DMSO, or DMF, which allows for easy sample preparation for fluorescence-based assays.

The subject compounds selectively and rapidly stain both live and dead cells with a high affinity for nucleic acids (e.g., DNA). The compounds of the invention are remarkably non-toxic, making them particularly useful in applications involving live cells.

The absorbance spectrum for compounds of the invention provide an excitation maximum ranging from 400-700 nm and a fluorescence emission spectrum extending into the near IR region of the electromagnetic spectrum (e.g., >660 nm). The subject compound also are relatively stable to photobleaching and can remain intensely fluorescent even after repeated exposure to the intense illumination, such as by an epifluorescence microscope.

Representative methods for preparing the anthraquinone compounds of the invention are described in the Examples provided herein.

Applications and Methods of Use

The compounds provided herein may be used in various fluorescence-based technologies and assays. The compounds of the invention may be used to directly stain or label a sample so that the sample can be identified or quantitated. For example, such compounds may be added as part of an assay for a biological target analyte or as a detectable tracer element in a biological or non-biological fluid.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells may be single cells, including microorganisms, or multiple cells associated with other cells in two or three dimensional layers, including multicellular organisms, embryos, tissues, biofilms, and the like.

Alternatively, the sample is a solid. For example, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. The sample may also come from any solid tissue, which is disaggregated, to allow for a suspension of single cells to be labeled and tested on a flow cytometer. Alternatively, the sample is obtained from an environmental source such as soil, water, or air, or from an industrial source such as taken from a waste stream, a water source, a supply line, or a production lot. The sample can also include particles, such as particles labeled with one or more types of nucleic acid molecules. The sample may be or contain bare nuclei.

The sample is present on or in solid or semi-solid matrix. The matrix may be a membrane. The matrix may an electrophoretic gel, such as is used for separating and characterizing nucleic acids or proteins, or is a blot prepared by transfer from an electrophoretic gel to a membrane. The matrix may be a silicon chip or glass slide, and the analyte of interest has been immobilized on the chip or slide in an array (e.g., the sample includes proteins or nucleic acid polymers in a microarray). In other embodiments, the sample is present in a solvent (e.g., organic solvent). In yet another aspect, the matrix is a microwell plate or microfluidic chip, and the sample is analyzed by automated methods, typically by various methods of high-throughput screening, such as drug screening.

The present compounds generally are utilized by combining the compound with a sample of interest under conditions selected to yield a detectable optical response. The compound typically associates in a non-covalent manner to form a complex with an element of the sample, or is simply present within the bounds of the sample or portion of the sample. The sample is then illuminated at a wavelength selected to elicit the optical response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

For biological applications, the compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar to ten millimolar or more. The optimal concentration is determined by systematic variation until satisfactory results with minimal background fluorescence are accomplished. In one embodiment, the compound may be used at a concentration of 1 nM to about 500 nM. In other embodiments, the compound may be used at a concentration of about 500 nM to about 1 µM; or about 1 µM to about 500 µM; or about 500 µM to about 1 mM; or about 1 mM to about 10 mM; or about 10 mM to about 30 mM. In certain embodiments, assays are performed using a compound according to the invention in a concentration of 500 µM or less; or 100 µM or less; or 10 µM or less; or 5 µM or less; or 1 µM or less. Depending on the assay, it may be preferred to use a compound concentration of less than 10 µM (e.g. 1 or 5 µM).

The compounds are advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). The described compounds are generally non-toxic to living cells and other biological components, within the concentrations of use. Representative methods for evaluating cytotoxicity are provided in the Examples provided herein. The remarkably low toxicity exhibited by the subject compounds permits their use at higher concentrations than previously possible with other commercially available near IR DNA stains (e.g., anthraquinone-based stains, such as DRAQ5 (available from Biostatus Limited, UK)).

The compound is combined with the sample in any way that facilitates contact between the compound and the sample components of interest. Typically, the dye compound or a solution containing the compound is simply added to the sample. The compounds of the invention tend to be permeant to membranes of biological cells, and once inside viable cells are typically well retained. The present compounds can rapidly and effectively enter living cells, making them suitable for use in assays designed to probe living cells (e.g., cell cycle analysis). Treatments that permeabilize the plasma membrane, such as detergents or alcohols, electroporation, shock treatments or high extracellular ATP also can be used to introduce selected compounds into cells. Alternatively, selected compounds can be physically inserted into cells, e.g. by pressure microinjection, scrape loading, patch clamp methods, or phagocytosis.

Optionally, the sample is not washed after staining. The sample can be combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate of the present invention having spectral properties that are detectably distinct from those of the staining dye.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into flow cytometers, laser scanners, fluorescence microplate readers, standard or minifluorometers, or chromatographic detectors. Certain embodiments of the invention utilize dyes that are be excitable at or near wavelengths in regions that closely match the output of standard equipment (e.g., >660 nm).

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is analyzed using a flow cytometer, examination of the sample, optionally, can further include sorting portions of the sample according to their fluorescence response.

In one aspect, a method of determining whether a nucleic acid molecule is present in a sample is provided that involves contacting a sample with a compound of the invention. The presence of absence of a detectable optical response under the desired conditions will be indicative of the presence or absence of nucleic acid molecules in the sample.

In another aspect, a method of staining a sample containing nucleic acid is provided in which a sample is contacted with a compound, as described herein. An exemplary method involves combining a solution that contains a compound of the invention with a sample in a concentration sufficient to yield a detectable optical response under the desired conditions. Under the appropriate conditions, the anthraquinone-based compound can form a complex with nucleic acid (e.g., DNA) present in the sample, which generates a detectable optical response under the desired conditions.

In certain embodiments, the sample is a biological sample. The biological sample can include live cells, fixed cells, or fixed and permeabilized cells, or free cell nuclei. The cells may be treated with a cell fixative reagent, a cell permeabilizing reagent, or a combination of a cell fixative reagent and cell permeabilizing reagent.

As discussed above, the described compounds have an affinity for nucleic acid molecules and can form a complex with nucleic acids, which can be detected optically.

The complex may be formed with a compound that is in a free base form or in a salt form. The compound may be in a salt form that includes a counterion, such as, for example, Cl—, Br—, I—, $ClO_4$— OAc—, $SO_4$—, tartrate, or citrate. In certain embodiments, it may be desirable to use a chloride or acetate salt of the compound.

The complex may be formed by non-covalently associating a compound of the invention with a nucleic acid molecule. The nucleic acid molecule can be a nucleic acid polymer, such as, for example, DNA or RNA. Alternatively, the nucleic acid molecule can be an oligonucleotide, a chromosome or a fragment thereof.

In certain embodiments, the complex is formed when a compound, as described herein, associates with double-stranded DNA. In certain embodiments, the compound selectively binds double-stranded DNA over other types of nucleic acid polymers (e.g., single-stranded DNA or RNA).

The complex may be present in a biological sample wherein the biological sample includes cells, or the isolated nuclei of cells. The cells may be live or dead cells. In certain embodiments, the biological sample includes live cells. The compounds provided herein have application for both fixed specimens and viable cells.

The complex may be formed by association of a compound, as described herein, with a nucleic acid molecule that is present in the nucleus of a eukaryote. Alternatively, or in addition, the nucleic acid molecule is present in the nucleus of a prokaryote.

The complex may be present in an aqueous solution (e.g., a buffer or biological fluid). Alternatively, the complex may be present in a polymeric gel or in an electrophoretic matrix or in organic solvent, such as DMSO or DMF.

Prior to association with a nucleic acid molecule, the compound may be non-fluorescent or dimly fluorescent. Once the compound complexes with a nucleic acid molecule, the dye becomes fluorescent or its fluorescence increases and may be optically detected. The ratio of compound:nucleic acid molecule that elicits an optical response may be determined empirically. The optimal amount of compound can be determined empirically with each cell type, buffer or media, cell concentration, testing procedure and testing platform used, however, typically one nanomolar to one millimolar to ten millimolar or more of compound is used to produce a detectable optical signal.

The compounds of the invention can be used in a biological assay. The compound may be present in an unbound form or may be associated with a nucleic acid molecule. The nucleic acid molecule may be free in solution or contained with a biological material, such as a cell. Methods are provided to determine the presence of nucleic acid molecules in a sample. Generally, the method involves providing a biologically compatible solution of the compound and then treating a sample (e.g., a biological material or cells) that contains or is thought to contain nucleic acid molecules with the solution. The sample may include live cells, fixed cells, eukaryotic cells, prokaryotic cells, biological fluids, isolated cell nuclei, or tissue. The sample may include a nucleic acid polymer (e.g., DNA or RNA), nucleotides, or nucleosides. In certain embodiments, the sample includes double-stranded DNA. After sufficient time for the compound to complex with nucleic acids in the sample, the sample is excited with a light source (e.g., a laser). Due to its optical properties, the compound can emit a fluorescence signal upon excitation. Preferably, the light source provides photons of a wavelength that fall within the absorption wavelength range of the compound (e.g., 400-700 nm). Compounds of the invention typically emit light in the IR region of the electromagnetic spectrum and more typically in the near IR region of the spectrum.

Also provided is a method of staining a biological sample containing nucleic acids. A biological sample that contains or is thought to contain nucleic acid molecules is combined with a compound of the invention. The biological sample may be in solution. Further, the compound may be present in a concentration sufficient to yield a detectable optical response under the desired conditions.

The sample may include a combination of the compound and other fluorophores or dyes. For example, additional compound(s) may be present that emit in the UV or visible region of the spectrum upon excitation with an appropriate light source. The fluorescence spectra of the compounds described herein, by virtue of their relatively long emission wavlengths, make the compounds particularly useful in multiplex applications with fluorophores that emit in the UV or visible portion of the spectrum.

Methods for detecting the presence of nucleic acids in a sample may further include quantification of the nucleic acid detected.

The methods described herein may utilize live cells. Alternatively, these methods may utilize dead or fixed cells. Yet other methods utilize a combination of live and dead cells, fixed cells, permeabilized cells, and/or free cell nuclei. Cells may be treated with a cell fixative reagent, or a cell fixative reagent combined with a cell permeabilizing reagent, or a cell permeabilizing reagent.

The cells may be suspended in a fluid (e.g., a biological fluid or an aqueous fluid, such as buffer or water) or may be in a solid form, such as cells adherent to plates, coverslips, dishes, flasks, or solid tissue samples that have been disaggregated.

For labeling of living cells, a compound, as described herein, is added to a sample containing living cells. The sample can include cells suspended in a buffer or media, or cells adherent to a glass or plastic surface, bathed in a buffer or media. For flow cytometry analysis, the compound can be added to the buffer or media containing living cells, incubated, and data acquired without washing the dye out of the sample. To ensure analysis is performed on living cells, a dead cell dye or a live cell dye may be included in the testing for gating out of dead cells or gating on living cells.

In another aspect, methods of quantifying nucleic acid content in live cells are provided. The compound is combined with a sample (e.g., a biological fluid or a sample of cells) that contains nucleic acid molecules (e.g., DNA) to form a mixture. The sample may be in the form of a suspension or solution. The sample may be processed to adhere the cells to a surface (e.g., plate, slide, cover slip, or the like). The sample is incubated for a sufficient amount of time for the compound to associate with the nucleic acid in the sample (e.g., about 5-15 minutes or up to one hour or more). The incubated sample is then illuminated with an appropriate wavelength of light to generate a detectable optical response resulting from the presence of a complex of the compound with a nucleic acid molecule in the sample. Illumination may be achieved by the use of a laser, diode laser, mercury arc lamp or other such focused light source. The optical response can be detected to determine presence of nucleic acid molecules in the sample. Detection may be achieved using instrumentation and methods well known to those skilled in the art, such as, for example, flow cytometry, confocal laser scanning microscopy, and imaging (e.g., high content image analysis). Methods of quantifying nucleic acid content in cells using fluorophores are well known to those skilled in the art.

In another aspect, methods for evaluating DNA content for cell cycle analysis are provided. The unique fluorescence properties and ability of the compounds of the invention to enter viable cells make these compounds particularly useful in cell cycle analysis studies. Flow cytometry can be used with the compounds of the invention to differentiate cells in various stages of the cycle DNA content for cell cycle analysis using flow cytometric methods are well known to those skilled in the art (see, e.g., Current Protocols in Cytometry, 7.0.1-7.27.7 (2004)).

In yet another aspect, detection of nucleic acid molecules in a sample may be accomplished using imaging. A compound, as described herein, is combined with a sample (e.g., a biological fluid or a sample of cells) that contains or is thought to contain nucleic acid molecules (e.g., DNA) to form a mixture. The solution is incubated for a sufficient amount of time for the compound to associate with the nucleic acid in the sample (about 5 minutes to 15 minutes to one hour or more). The incubated sample is then illuminated with an appropriate wavelength of light to generate a detectable optical response resulting from the presence of a complex of the compound with a nucleic acid molecule in the sample. Illumination may be achieved by the use of a laser diode laser, mercury arc lamp or other such focused light source. The optical response can be detected to determine presence and location of nucleic acid molecules in the sample and may be achieved using detection methods well known to those skilled in the art. Detection may be achieved by imaging to determine the presence and location of nucleic acid molecules in a sample. Other uses of imaging analysis using the compounds of the invention include nuclear localization and DNA profile in whole cells or tissues; quantifying the percent of cells containing 2N and 4N DNA content based on relative fluorescence intensity; detecting nuclear or chromosomal morphology and orientation in cells labeled with these compounds to indicate apoptosis (e.g., nuclear condensation and blebbing) or stage of mitosis, respectively; detecting micronuclei formation in labeled cells to measure genotoxicity during drug screening and discovery; and use of labeled nucleic acids in cells in automated imaging and analysis for cell demarcation by either nuclear or whole cell segmentation algorithms.

In yet another aspect, a method of detecting the presence of fixed cells in a sample is provided. A compound, as described herein, can be combined with a sample to form a mixture. The sample can include fixed cells, where the fixed cells contain nucleic acid molecules (e.g., DNA). Alternatively, the described compounds can be added to live cells in combination with a fixative agent. The mixture is incubated for a sufficient amount of time for the compound to associate with the nucleic acid in the sample. The incubated sample is illuminated with an appropriate wavelength to generate a detectable optical response. Detection of the response indicates the presence and location of the nucleic acid material in the cells.

The compounds of the invention may be used in high content screening (HCS), for example, to evaluate various cell health parameters in an automated format. In certain embodiments, the described compounds can be combined with a nuclear segmentation tool to measure cytotoxicity in cells. Cytotoxicity is a multi-parametric process resulting in plasma membrane permeability. The subject compounds can behave as an impermeant dye in healthy cells and can become permeant when the plasma membrane of cells is compromised.

The stains provided herein are amenable to fixation and permeabilization and allow for multiplexing with other biomarkers of cytotoxicity. The optical properties of the disclosed compounds make it possible to use the described compounds in multiplex assays in combination with multiple fluorophores and using several types of lasers. The disclosed compounds exhibit infrared excitation and emission bands, rendering them applicable for use in combination with many other fluorophores emitting at shorter wavelengths. For example, longer wavelength emission in the near IR region allows for multiplexing with fluorochrome-labeled antibodies. Alternatively, shorter wavelengths of light may be used to excite these compounds, increasing the flexibility of their use. Longer wavelength excitation and emission wavelengths also allow the end user to avoid background associated with endogenous cellular fluorescence, particularly at excitation wavelengths in the UV to blue range of the spectrum.

Additional applications of the disclosed fluorescent compounds include labeling of particles and bare nuclei. The particles optionally may be labeled with nucleic acids. In one embodiment, labeled particles and nuclei may be used for instrument set-up and calibration purposes (e.g., set-up and calibration in the near-IR detection region of an instrument).

The compounds of the invention may be incorporated into kits that facilitate the practice of various assays. The kits may be packaged with the compound in a dry form or with the compound in solution. The kits may optionally further include one or more buffering agents, typically present as an aqueous solution, sample preparation reagents, additional detection reagents, organic solvent, other fluorescent detection probes, standards, microspheres, specific cell lines, antibodies and/or instructions for carrying out an assay. Additional optional agents include components for testing of other cell functions in conjunction with the compound.

The following examples are given for the purpose of illustrating the invention and shall not be construed as being a limitation on the scope of the invention or claims.

EXAMPLES

Example 1

Synthesis of Compound 1

A mixture of 50 mg of 1,5-diamino-4,8-dihydroxyanthra-9,10-quinone, and 122 mg of α,α'-dibromo-p-xylene in 2 mL of DMF was heated at 85° C. for 1.5 hours to generate the crude benzyl bromide (Compound 1) after the removal of all volatile components.

Compound 1

Example 2

Synthesis of Compound 2

The crude benzyl bromide (Compound 1) was dissolved in 5 mL of dimethylamine solution (2.0 M in methanol) and stirred at room temperature overnight. Volatile components were evaporated under reduced pressure and the product (Compound 2) was purified on a LH-20 column and then HPLC. MS (ESI$^+$) [m/z]: 565.8 [M+H]$^+$.

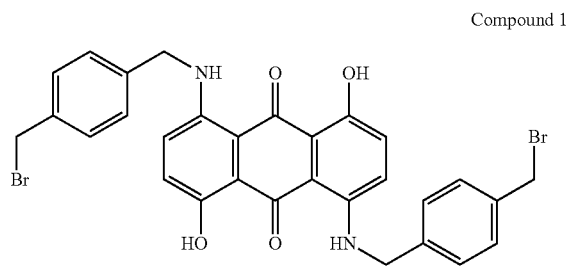 [SMILES: O=C1c2c(O)ccc(NCc3ccc(CBr)cc3)c2C(=O)c2c(O)ccc(NCc3ccc(CBr)cc3)c21]

Compound 2

Example 3

Synthesis of Compound 3

A mixture of 3-chloro-1-propanol (10 g), and sodium azide (13.7 g) in water (50 mL) was heated at 90° C. overnight. Compound 3 was obtained by ether extraction.

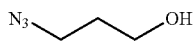

Compound 3

Example 4

Synthesis of Compound 4

To a solution of Compound 3 (935 mg) in pyridine (10 mL) was added p-toluenesulfonyl chloride (1.9 g) at 0° C., and the mixture was stirred at room temp for 2 hours. The mixture was diluted with water and extracted with ether to yield the crude tosylate (Compound 4).

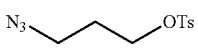

Compound 4

Example 5

Synthesis of Compound 5

The crude tosylate (Compound 4) was treated with 20 mL of dimethylamine solution (2.0 M in methanol) at room temp for 4 hours. Excess of dimethylamine was removed by bubbling nitrogen and water (30 mL) was added and extracted with ether. The organic layer was washed vigorously with 30 mL of 1N HCl solution and the aqueous layer was lyophilized to yield the product (Compound 5).

Compound 5

Example 6

Synthesis of Compound 6

A mixture of 1,5-diamino-4,8-dihydroxyanthra-9,10-quinone (50 mg) and propargyl bromide (0.1 mL) in DMF (2 mL) was heated at 90° C. for 2 hours. Volatile components were evaporated under reduced pressure to give the crude alkyne (Compound 6).

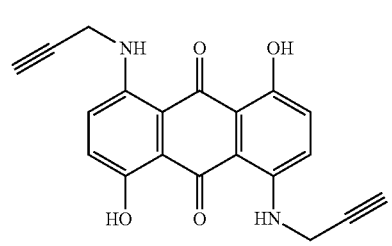

Compound 6

Example 7

Synthesis of Compound 7

The crude alkyne (Compound 6) was stirred in a mixture of copper(I) iodide (36 mg), N,N-diisopropylethylamine (0.33 mL), Compound 5 (311 mg), water (1 mL), and ethanol (1 mL) at room temp overnight. Volatile components were evaporated under reduced pressure and the product (Compound 7) was purified on a LH-20 column and then HPLC. MS (ESI+) [m/z]: 604.0 [M+H]+.

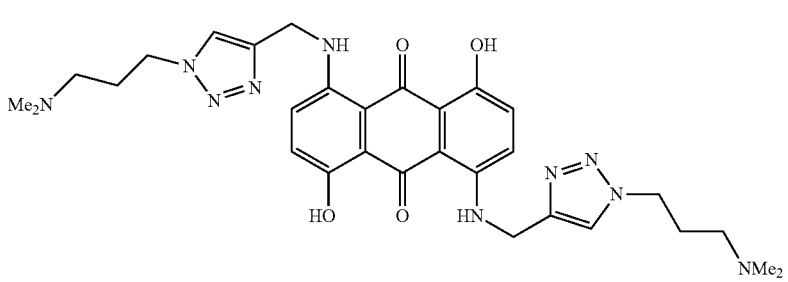

Compound 7

Example 8

Synthesis of Compound 8

To bromoacetyl chloride (466 mg) in diethyl ether (10 mL) was added N,N-diethylethylenediamine (322 µL) in diethyl ether (2 mL) at −5° C., and the mixture was stirred at room temp overnight. Removal of ether yielded the product (Compound 8).

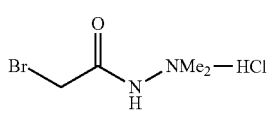

Compound 8

Example 9

Synthesis of Compound 9

A mixture of 1,5-diamino-4,8-dihydroxyanthra-9,10-quinone (500 mg), Compound 8 (~4.6 g), and sodium iodide (2.78 g) in DMF (24 mL) was heated at 100° C. for 3 hours. DMF was removed under reduced pressure. The product (Compound 9) was purified with a silica gel column and HPLC (pH 7 ammonium acetate buffer solution). Compound 9a was obtained in acetate form after HPLC purification. HCl salt (Compound 9b) was obtained by adding 10 eq. 1N HCl and then lyophilization. Free amine form (Compound 9) was obtained via repeated lyophilization (2-3 times) of Compound 9a. MS (ESI$^+$) [m/z]: 399.2 [M+H]$^+$.

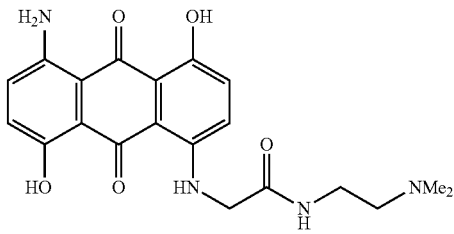

Compound 9

Example 10

Synthesis of Compound 10

To bromoacetyl chloride (500 mg) in diethyl ether (8 mL) was added 1-methylpiperazine (319 mg) in diethyl ether (2 mL) at 0° C., and the mixture was stirred at room temp for 4 hours. Removal of ether by rotary evaporation gave the crude product (Compound 10).

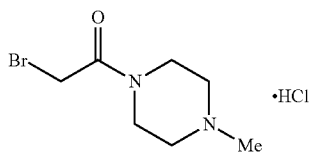

Compound 10

Example 11

Synthesis of Compound 11

A mixture of 1,5-diamino-4,8-dihydroxyanthra-9,10-quinone (50 mg), and Compound 10 (~800 mg) in 3 mL of N,N-dimethylacetamide (DMA) was heated at 100° C. for 3 hours. DMA was removed under reduced pressure. The product (Compound 11) was purified on a LH-20 column and then HPLC. MS (ESI$^+$) [m/z]: 411.3 [M+H]$^+$.

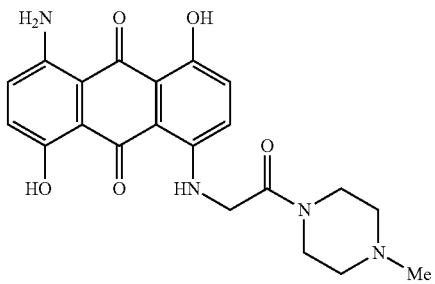

Compound 11

Example 12

Synthesis of Compound 12

A solution of N-Boc-ethylenediamine-HCl salt (707 mg), and diisopropylethylamine (1.38 mL) in dichloromethane (5 mL) was added to bromoacetyl chloride (0.3 mL) in 2 mL of dichloromethane at 0° C. After stirring at 0° C. for 1 hour and room temperature for 2 hours, ethyl acetate (50 mL) was added and the organic layer was washed by water and brine, dried over MgSO$_4$ to yield the product (Compound 12).

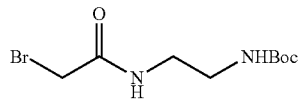

Compound 12

Example 13

Synthesis of Compound 13

A mixture of 1,5-diamino-4,8-dihydroxyanthra-9,10-quinone (50 mg), and Compound 12 (300 mg) in DMA (2 mL) was heated at 100° C. for 5 hours. DMA was removed under reduced pressure. The product (Compound 13) was purified on a silica gel column with ethyl acetate and chloroform. MS (ESI$^+$) [m/z]: 471.3 [M+H]$^+$.

Compound 13

Example 14

Synthesis of Compound 14

To Compound 13 (30 mg) in dichloromethane (2 mL) was added trifluoroacetic acid (1 mL) at 0° C., and the mixture was stirred at room temp for 3 hours. Volatile components were evaporated under reduced pressure. The product (Compound 14) was purified on a LH-20 column and then HPLC. MS (ESI$^+$) [m/z]: 371.0 [M+H]$^+$.

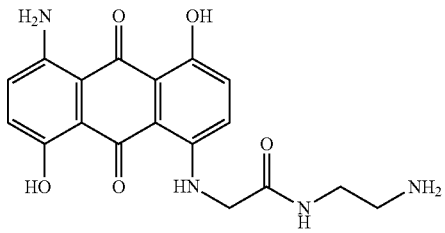

Compound 14

Example 15

Synthesis of Compound 15

To N,N-diethylethylenediamine (344 mg) in 6 mL of dichloromethane at −10° C. bromoacetyl chloride (466 mg) was added. The mixture was then stirred at room temp for 5 hours. Removal of dichloromethane gave crude product (Compound 15).

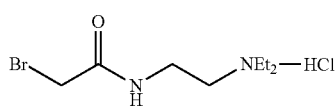

Compound 15

Example 16

Synthesis of Compound 16

A mixture of 1,5-diamino-4,8-dihydroxyanthra-9,10-quinone (80 mg), and Compound 15 (~800 mg) in DMA (2 mL) was heated at 90° C. for 3 hours. DMA was removed under reduced pressure. The product (Compound 16) was purified on a silica gel column with methanol and chloroform, and on a LH-20 column with water, methanol, and acetic acid. MS (ESI$^+$) [m/z]: 427.3 [M+H]$^+$.

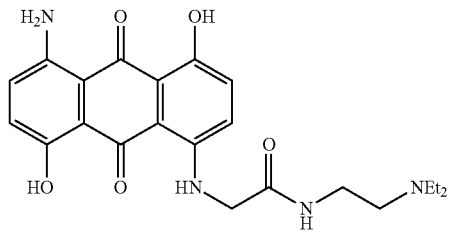

Compound 16

Example 17

Synthesis of Compound 17

To N,N,N'-trimethylethylenediamine (151 mg) in 3 mL of dichloromethane at 0° C. bromoacetyl chloride (123 μL) was added and the mixture was stirred at 0° C. for 30 minutes and then at room temp for 3 hours. Dichloromethane was removed under reduced pressure to yield crude product (Compound 17).

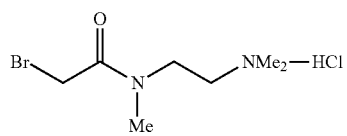

Compound 17

Example 18

Synthesis of Compound 18

A mixture of 1,5-diamino-4,8-dihydroxyanthra-9,10-quinone (50 mg), and Compound 8 (~380 mg) in DMF (3 mL) was heated at 100° C. for 1.5 hours. DMF was removed under reduced pressure. The product (Compound 18) was purified on a LH-20 column with water, methanol, and acetic acid. MS (ESI$^+$) [m/z]: 413.4 [M+H]$^+$.

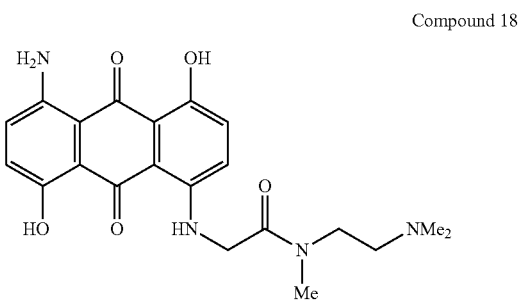 [SMILES: CN(C)CCN(C)C(=O)CNc1ccc(O)c2c1C(=O)c1c(O)ccc(N)c1C2=O]

Compound 18

Example 19

Synthesis of Compound 19

A mixture of 1,8-diamino-4,5-dihydroxyanthra-9,10-quinone (50 mg), and Compound 8 (~450 mg) in DMF (3 mL) was heated at 100° C. for 1.5 hours. DMF was removed under reduced pressure. The product (Compound 19) was purified on a LH-20 column with water, methanol, and acetic acid. MS (ESI$^+$) [m/z]: 399.4 [M+H]$^+$.

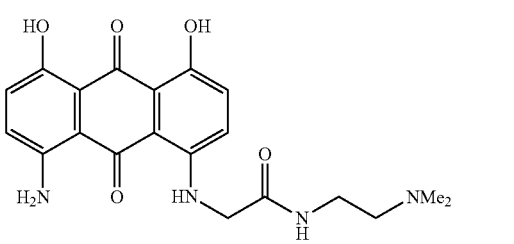

Compound 19

Example 20

Synthesis of Compound 20

A mixture of 1,4-diamino-5,8-dihydroxyanthra-9,10-quinone (30 mg), and Compound 8 (~260 mg) in DMF (3 mL) was heated to 100° C. for 1.5 hours. DMF was removed under reduced pressure. The product (Compound 20) was purified on a LH-20 column with water, methanol, and acetic acid. MS (ESI$^+$) [m/z]: 399.4 [M+H]$^+$.

Compound 20

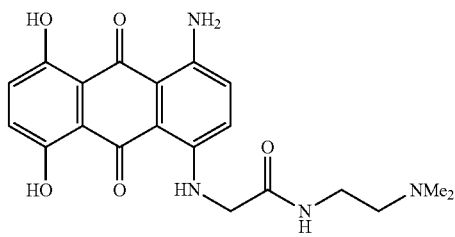

Example 21

Synthesis of Compound 21

To Compound 9 (5 mg) in 1 mL of DMF, 0.5 mL of iodomethane was introduced and the mixture was stirred at room temp for 30 min Volatile components were evaporated under reduced pressure and the product (Compound 21) was purified on a LH-20 column with water, methanol, and acetic acid. MS (ESI$^+$) [m/z]: 413.5 [M+H]$^+$.

Compound 21

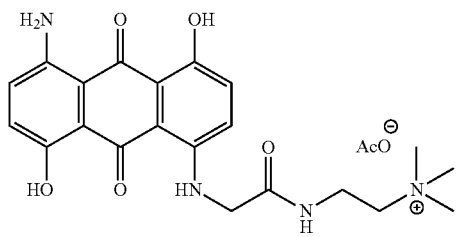

Example 22

Synthesis of Compound 22

A mixture of 1,5-diamino-4,8-dihydroxyanthra-9,10-quinone (100 mg), and bromoacetonitrile (266 mg) in DMF (3 mL) was heated to 120° C. for 3 hours. Volatile components were evaporated under reduced pressure to yield the crude cyanide (Compound 22).

Compound 22

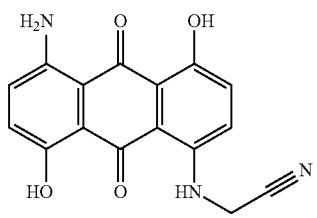

Example 23

Synthesis of Compound 23

The crude cyanide (Compound 22) was treated with methanol (2 mL) and 4.0 M HCl in 1,4-dioxane (2 mL). The mixture was stirred at room temp for 18 hours. Volatile components were evaporated under reduced pressure to give crude product (Compound 23).

Compound 23

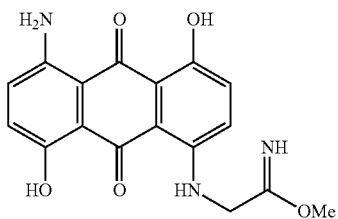

Example 24

Synthesis of Compound 24

The crude product of Compound 23 was treated with 4 mL of acetic acid and 0.5 mL of N,N-dimethylethylenediamine and heated to 60° C. for 8 hours. Volatile components were evaporated under reduced pressure, and the product (Compound 24) was purified on a LH-20 column with water, methanol, and acetone and a reversed phase column MS (ESI$^+$) [m/z]: 398.5 [M+H]$^+$.

Compound 24

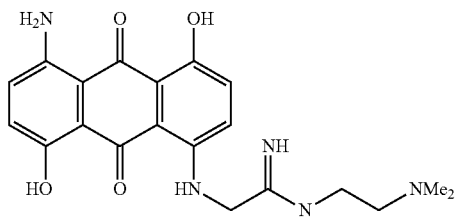

Example 25

Synthesis of Compound 25

A mixture of 4-(2-aminoethyl)morpholine (130 μL), and bromoacetyl chloride (83 μL) in dichloromethane (3 mL) was stirred at 0° C. for 30 minutes and at room temp for 3 hours. Removal of dichloromethane by rotary evaporation gave crude product (Compound 25).

Compound 25

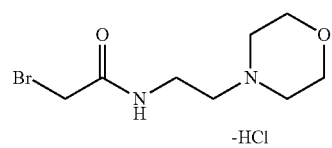

Example 26

Synthesis of Compound 26

A mixture of 1,5-diamino-4,8-dihydroxyanthra-9,10-quinone (50 mg), and Compound 25 (~280 mg) in DMF (3 mL) was heated at 100° C. for 3 hours. DMF was removed under reduced pressure. The product (Compound 26) was purified on a LH-20 column with methanol. MS (ESI⁺) [m/z]: 441.3 [M+H]⁺.

and chloroform, and on a LH-20 column with water, methanol, and acetic acid. MS (ESI⁺) [m/z]: 454.3 [M+H]⁺.

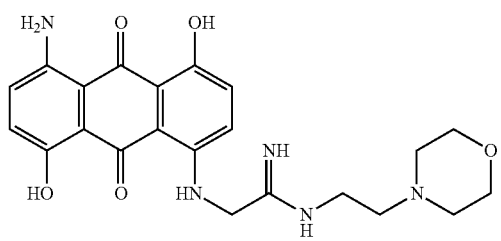

Compound 26

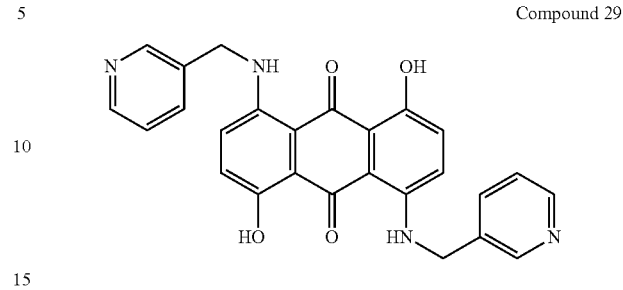

Compound 29

A mixture of 1-(3-aminopropyl)imidazole (119 μL), and bromoacetyl chloride (83 μL) in dichloromethane (3 mL) was stirred at 0° C. for 30 minutes and at room temp for 3 hours. Removal of dichloromethane by rotary evaporation gave crude product (Compound 27).

Example 30

Synthesis of Compound 30

A mixture of 1-(2-aminoethyl)pyrrolidine (126 μL), and bromoacetyl chloride (83 μL) in dichloromethane (5 mL) was stirred at 0° C. for 30 minutes and at room temp for 3 hours. Removal of dichloromethane by rotary evaporation gave crude product (Compound 30).

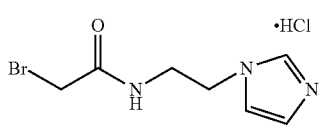

Compound 27

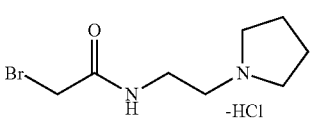

Compound 30

Example 28

Synthesis of Compound 28

A mixture of 1,5-diamino-4,8-dihydroxyanthra-9,10-quinone (50 mg), and Compound 27 (~270 mg) in DMF (3 mL) was heated at 100° C. for 2 hours. DMF was removed under reduced pressure. The product (Compound 28) was purified on an LH-20 column with methanol. MS (ESI⁺) [m/z]: 436.3 [M+H]⁺.

Example 31

Synthesis of Compound 31

A mixture of 1,5-diamino-4,8-dihydroxyanthra-9,10-quinone (50 mg), and Compound 30 (~260 mg) in DMF (3 mL) was heated at 100° C. for 2 hours. DMF was removed under reduced pressure. The product (Compound 31) was purified on a LH-20 column with methanol. MS (ESI⁺) [m/z]: 425.4 [M+H]⁺.

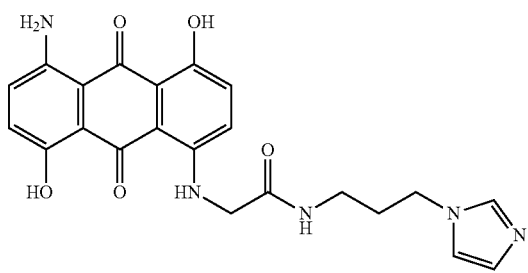

Compound 28

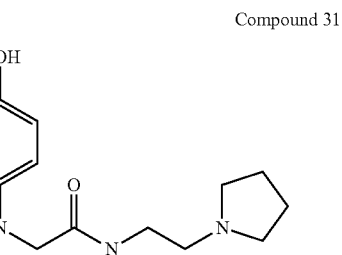

Compound 31

Example 29

Synthesis of Compound 29

A mixture of 1,5-diamino-4,8-dihydroxyanthra-9,10-quinone (50 mg), and 2-(bromomethyl)pyridine-HBr salt (140 mg) in DMF (3 mL) was heated at 100° C. for 3 hours. DMF was removed under reduced pressure. The product (Compound 29) was purified on a silica gel column with methanol

Example 32

Synthesis of Compound 32

A mixture of 1,8-diamino-4,5-dihydroxyanthra-9,10-quinone (50 mg), and Compound 27 (~260 mg) in DMF (4 mL) was heated at 100° C. for 2 hours. DMF was removed under reduced pressure. The product (Compound 32) was purified on a LH-20 column with methanol. MS (ESI⁺) [m/z]: 436.3 [M+H]⁺.

Compound 32

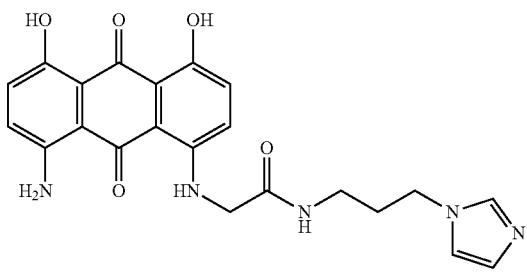

Example 33

Synthesis of Compound 33

A mixture of 3-amino-1-Boc-azetidine (250 mg), bromoacetyl chloride (121 μL), and triethylamine (202 μL), in dichloromethane (5 mL) was stirred at 0° C. for 30 minutes and at room temp for 1 hour. The mixture was diluted with dichloromethane (20 mL), and the combined organic layer was washed with water and brine, dried over MgSO₄, and concentrated to dryness to yield Compound 33.

Compound 33

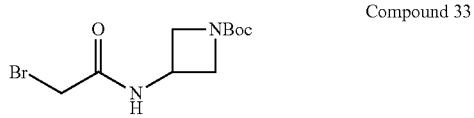

Example 34

Synthesis of Compound 34

A mixture of 1,5-diamino-4,8-dihydroxyanthra-9,10-quinone (50 mg), and Compound 33 (~260 mg) in DMF (3 mL) was heated at 100° C. for 2 hours. DMF was removed under reduced pressure to give the crude product (Compound 34).

Compound 34

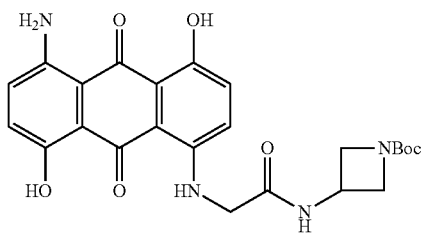

Example 35

Synthesis of Compound 35

The crude product (Compound 34) was treated with dichloromethane (3 mL) and trifluoroacetic acid (1 mL) at 0° C. and stirred for 1.5 hours. Volatile components were evaporated under reduced pressure, and the product (Compound 35) was purified on a LH-20 column with methanol. MS (ESI⁺) [m/z]: 383.4 [M+H]⁺.

Compound 35

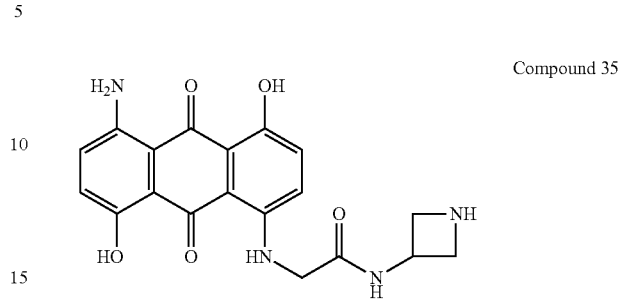

Example 36

DNA Staining of Live Cells and DNA Content Cell Cycle Analysis Using Flow Cytometry Live Jurkat cells are suspended at 5×10⁵ cells/ml in each RPMI media with 10% Fetal Bovine Serum (FBS) and Hanks Balanced Salt Solution (HBSS). A compound (e.g., Compound 9 or a salt thereof) is added to each of one mL cell suspensions at concentrations 1 μM, 5 μM, 10 μM, and 20 μM, and then incubated at 37° C. or room temperature for 30 minutes while protected from light. Cells are run through a Becton Dickinson (BD) LSRII Flow Cytometer. Forward Scatter (FS) versus Side Scatter (SS) dual parameter plot is used to gate main cell population. Fluorescence is collected using three lasers: 488 nm excitation laser with 670/14, 720/20 and 787/42 bandpass emission filter, 532 nm excitation laser with 585/42 and 780/60 bandpass emission filters, and 633 nm excitation laser with 695/40, and 787/42 bandpass emission filters. Collection of at least 10,000 events at flow rate of ~200 events/second. The data is further analyzed using MODFIT LT Flow Cytometry Modeling Software from Verity Software House, Inc. to evaluate the ratio of G2/G1 and the % CV of G1 phase.

DNA content analysis in living cells is expected to produce variable results. Depending on the cell type, the % CV of the mean DNA content of a uniform cell population may vary from between 5%-10%. Although there is no formal consensus regarding the acceptable maximal CV value for the mean DNA content of the G0G1 phase, the % CV of normal diploid cells in a histogram generally is <8%. The CV of a tumor may be higher due to the presence of multiple tumor subpopulations. However, tumor CVs of <8% are recommended for useful S-Phase determinations (Cytometry, Vol. 14 (5), 1993, page 474).

Linearity is the observed ratio between the DNA Diploid G2M and G0G1 positions. The ratio normally is about two, but this ratio may deviate from the ideal value even under normal conditions (see, MODFIT LT User Guide, June 2000).

Compound 9 was evaluated according to the described procedure and found an effective stain for DNA and was excited by all three lasers with emission in the far red and near-IR regions of the spectrum. Cell histograms were collected for each of the samples tested and analyzed to determine % CV of G1-phase and G2/G1 ratios. DNA cell cycle histograms provided information about the G0G1 phase, S phase, and G2M phase, as obtained on the live cell gate, with all concentrations of the compound, and in both media and HBSS at 37° C. and room temperature. Further analysis using MODFIT Software showed that the tested compound stained live cells for DNA cell cycle analysis with % CV of G1-phase <8%, and G2/G1 ratios indicating linearity of staining.

Figure 2:
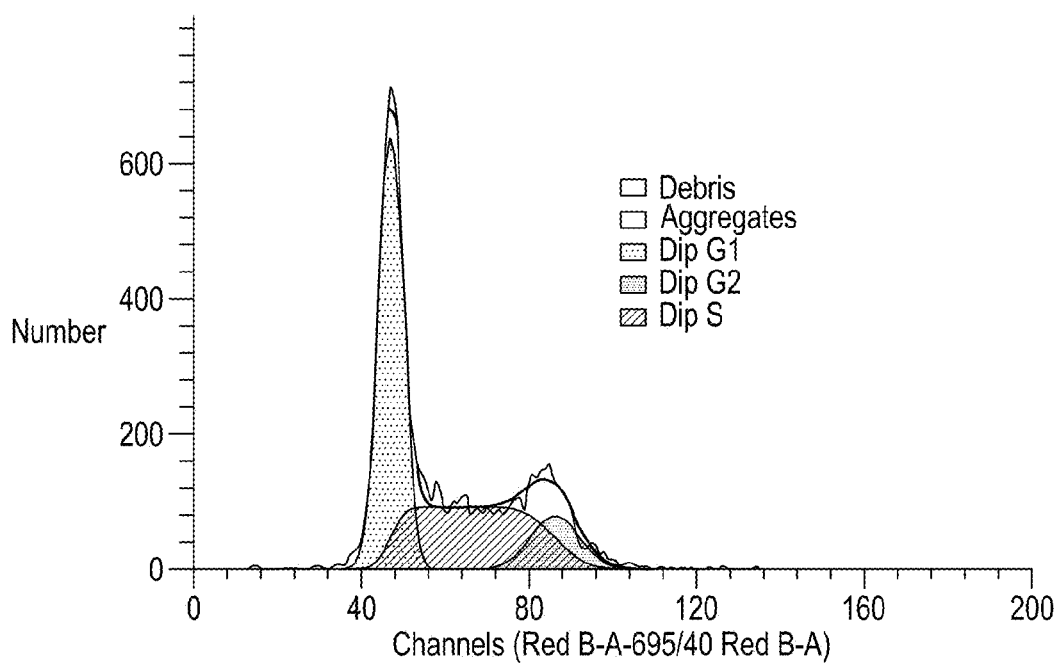
FIG. 2 shows the cell cycle histogram generated from the data shown in FIG. 1, analyzed using MODFIT Software.

FIG. 1 shows a typical cell cycle histogram for live Jurkat cells suspended in RPMI media+10% FBS treated with 511M Compound 9 and incubated for 30 minutes at 37° C., acquisition using 633 nm excitation and 695/40BP emission. The data from FIG. 1 was analyzed using MODFIT Software and is shown in FIG. 2. The % CV and G2/G1 ratios were within the limits of the cell cycle model (Table 1).

TABLE 1

Comparison of Flow Cytometry Results for DNA Staining of Live Jurkat cells

| Concentration of Compound (µM) | Solution Contents | Temperature | G2/G1 ratio | % CV |
|---|---|---|---|---|
| 1 | RPMI media | 37° C. | 1.91 | 7/12 |
| 5 | RPMI media | 37° C. | 1.83 | 6.10 |
| 10 | RPMI media | 37° C. | 1.82 | 6.12 |
| 10 | RPMI media | room temperature | 1.82 | 6.13 |
| 10 | HBSS buffer | 37° C. | 1.84 | 7.85 |
| 10 | HBSS buffer | room temperature | 1.83 | 7.32 |
| 20 | RPMI media | 37° C. | 1.87 | 7.76 |

Example 37

DNA Staining of Live Cells Treated with RNase

Live Jurkat cells (human T-lymphocyte) were stained with Compound 9 with and without RNase treatment to assess DNA selectivity of the compound. Live Jurkat cells were suspended at $5\times10^5$ cells/ml in each RPMI media with 10% FBS. The dye was added to each of one mL cell suspensions at concentrations 5 µM and 10 µM. Duplicate conditions (dye concentration and incubation temperature) were tested. RNase was added to one test and incubated along with the dye. The other test was left untreated (no RNase present). The samples were incubated at 37° C. or room temperature for 30 minutes while protected from light. Cells were run through a Becton Dickinson (BD) LSRII Flow Cytometer, as described in Example 36. The DNA cell cycle histograms were typical, demonstrating G0G1 phase, S phase, and G2M phase, as obtained on the live cell gate, under all conditions tested. Addition of RNase gave equivalent results but did not improve the results, suggesting that the compound is DNA selective.

Example 38

DNA Staining of Live Cells (Diluted Samples) and DNA Content Cell Cycle Analysis Using Flow Cytometry Aliquots of a compound of the invention (e.g., Compound 9 or a salt thereof) are diluted to a concentration of 5 mM in de-ionized water (DI) or in DMSO. Live Jurkat cells are suspended at $5\times10^5$ cells/ml in each RPMI media with 10% FBS. Compound from each solution (DI and DMSO) is added to each of one mL cell suspensions at a concentration 5 µM and then incubated at 37° C. for 30 minutes while protected from light. Cells are run through a Becton Dickinson (BD) LSRII Flow Cytometer. Forward Scatter (FS) versus Side Scatter (SS) dual parameter plot is used to gate main cell population. Fluorescence is collected using two lasers: the 488 nm excitation laser with 695/40, and 780/60 bandpass emission filter, and using the 633 nm excitation laser with 780/60, 710/50, and 660/20 bandpass emission filters. Fluorescence is also collected with the 488 nm laser and the 530/30 and 575/26 bandpass emission filters to observe for any fluorescence spillover in these detectors. Collection of at least 10,000 events is performed at a flow rate of ~200 events/second. The data is analyzed to evaluate the ratio of G2/G1 and the % CV of G1 phase, as described herein. Compound 9 was evaluated using the described procedures and was effective as a DNA stain for use in DNA cell cycle analysis. The compound was excited by both lasers with emission in the far red and near-IR regions of the spectrum. Typical DNA content cell cycle histograms showed G0G1 phase, S phase, and G2M phase, as obtained on the live cell gate for all samples and conditions tested. Further analysis using MODFIT indicated that the compound effectively stains live cells for DNA cell cycle analysis, where the % CV of G1-phase <8%, and the observed ratio indicates linearity of staining (see, Table 2). Very little fluorescence was collected into the 530/30 and 575/26 bandpass filters, indicating that the compound could be used in combination with fluorophores emitting with these wavelengths. Table 2 summarizes data for live Jurkat cells suspended in RPMI media+10% FBS treated with 5 µM Compound 9 (as a 5 mM DMSO or DI solution).

TABLE 2

Comparison of Flow Cytommetry Results for DNA Staining of Live Jurkat cells

| Diluent | Excitation (nm) and Bandpass Emission Filer | G2/G1 ratio | % CV |
|---|---|---|---|
| DMSO | 488 + 695/40 | 1.88 | 7.38 |
| DMSO | 633 + 710/50 | 1.85 | 6.79 |
| DI | 488 + 695/40 | 1.89 | 7.15 |
| DI | 633 + 710/50 | 1.85 | 6.62 |

Example 39

Evaluation of Cell Health after DNA Staining of Cells

An ImageStream multispectral imaging flow cytometer is used to evaluate the live, apoptotic and mitotic rate of cycling Jurkat cells labeled with a compound of the invention (e.g., Compound 9 or a salt thereof). The platform produces high resolution brightfield, darkfield, and fluorescence images of cells prepared in suspension. IDEA analysis software I is used to quantify morphometric and photometric parameters for each cell based on the imaged collected. This technology combines the quantitative power of large sample sizes common to flow cytometry with the high information content present in microscopic images.

Live Jurkat cells are suspended at $5\times10^5$ cells/ml in each RPMI media with 10% FBS. The compound (in 5 mM DMSO) is added at a concentration of 5 µM and then the cells are incubated at 37° C. for 30 minutes while protected from light before acquiring on the ImageStream cytometer using 658 nm excitation and >660 nm emission. Apoptotic, mitotic, and interphase Jurkat cells are distinguished from each other using a combination of scatter, DNA intensity, and morphology-based parameters. Apoptotic cells with high laser scatter properties are gated on the Mean Pixel SSC histogram. Low scatter apoptotic events with low DNA content or textured nuclei are identified on the dye intensity versus bright detail intensity plot. This feature measures the intensity of small textures within the nuclear image, and condensed, fragmented nuclei have high values compared to the uniform nuclear staining pattern present in interphase nuclei. Compound 9 was evaluated in the described procedure, and the date indicated that 7.1% of the cells were dead following incubation with the dye, a number comparable to cultured Jurkat cells in media without treatment. Interestingly, mitotic cells had condensed chromosomes with high bright detail intensity values. These cells accounted for 1.9% of the live cell population, a number comparable to cultured Jurkat cells in media without treatment. The percentage of dead and apoptotic cells are consistent with those found in Jurkat cultures and demonstrate staining of the cells with the dye does not cause cell death.

Example 40

Imaging of Nuclear Proteins

Nuclear NF-kB is probed in cells stained with a nuclear stain using the ImageStream Imaging Flow Cytometer. When probing for nuclear proteins, it is critical to permeabilize the nuclear envelope sufficiently in order for the probing agent to gain entry into the nucleus. THP-1 monocytic cells are incubated in the presence or absence of 100 ng/mL LPS for 1 hour, fixed for 10 minutes at room temperature in 2% formaldehyde, and permeabilized with 0.1% saponin (the negative control), and three permeabilization buffers 0.1% TRITON X-100, 0.25% TRITON X-100, or methanol/0.1% TRITON X-100. NF-kB is probed with rabbit anti-p65 polyclonal antibody followed by anti-rabbit Alexa Fluor 488 dye (Invitrogen Corporation). The nucleus is counterstained with a dye (e.g., Compound 9 or a salt thereof). Nuclear translocation is quantitatively measured on the ImageStream Cytometer. Single cells with normal DNA content and high nuclear aspect ratios gated. Live, non-mitotic cells expressing NF-kB are gated separately (mitotic and apoptotic cells have high nuclear bright detail intensity values). To measure nuclear translocation, a similarity score is used, which correlates the NF-kB and nuclear images on a pixel-by-pixel basis. The nuclear image is measured with the dye, excited with the red 658 nm excitation laser and emission collected with >660 nm emission filter. The nuclear and NFkB images of untranslocated cells appear as opposites, and thus receive low or negative values. As NF-kB enters the nucleus, the images correlate more highly. Thus, the similarity score increases for translocated cells. In order to determine separation between the untreated and LPS-treated samples, the Rd statistical score is employed. The Rd measures the statistical separation between two populations, and is defined as the difference in the medians divided by the sum of the standard deviations between two comparison populations (in this case untreated vs LPS). The image for the tested compound is used as part of the similarity feature that measures 'degree of translocation' and to measure DNA content. Nuclear translocation is quantitatively measured and statistical discrimination between the untreated and LPS-treated samples is determined using the similarity score (using the nuclear staining with dye fluorescence and the NF-kB+Alexa Fluor 488 fluorescence). Compound 9 was evaluated using the described protocol. The similarity score was 0.04 with samples that used the 0.1% saponin permeabilization buffer, which was the negative control sample. The similarity score was 2.10 using the 0.1% TRITON X-100n permeabilization buffer; 2.00 using 0.25% TRITON X-100; and 2.26 using the methanol/0.1% TRITON X-100 permeabilization buffer. A DNA content histogram cycle (as measured with Compound 9 for the single cell population showed typical G0G1, S and G2M phase distributions and can be used to perform cell cycle, apoptosis, and nuclear translocation analysis in one experiment.

Example 41

Staining of Fixed Cells

Live Jurkat cells are fixed 70% cold ethanol and stored at −20° C. for one month. The cells are the washed in phosphate buffered saline (PBS) and resuspended in PBS at $5 \times 10^5$ cells/ml. Cells are labeled with a 5 µM solution of a compound according to the invention (e.g., Compound 9 or a salt thereof) at room temperature for 30 minutes and then run through two flow cytometers: A BD LSRII using 488 nm excitation and 695/40 nm emission and an Accuri C6 using 488 nm excitation and >670 nm emission, collecting 10,000 events at low flow rate. Markers are placed on the G0G1 and G2M peaks to look at % CV of the G0G1 peak and the ratio of G2M/G0G1.

Fixed cells suspended in PBS treated with 5 µM Compound 9 and incubated for 30 minutes room temperature, with 488 nm excitation and 695/40 bandpass fluorescence collection on a BD LSRII cytometer, yielded a typical DNA content cell cycle histogram. The % CV of the G0G1 peak was 6.0 and the ratio of G2M/G0G1 was 1.83. With 488 nm excitation and >670 nm bandpass fluorescence collection on the Accuri C6 cytometer, a typical cell cycle histogram was generated with % CV of the G0G1 peak of 5.9 and a ratio of G2M/G0G1 of 1.85. The results showed that Compound 9 is an effective stain for use in DNA content cell cycle analysis. Typical DNA content cell cycle histograms indicated G0G1 phase, S phase, and G2M phase, demonstrating that the tested compound can be used with fixed cells.

Example 42

DNA Staining of Live Cells and DNA Content Cell Cycle Analysis Using Flow Cytometry (Compound 19)

Live Jurkat cells are suspended at $5 \times 10^5$ cells/ml in each RPMI media with 10% FBS. Compound 19 is added to each of one mL cell suspensions at concentrations 5 µM, 10 µM, and 20 µM, and then incubated at 37° C. for 30 minutes while protected from light. Cells are run through the Becton Dickinson (BD) LSRII Flow Cytometer. Forward Scatter (FS) vs Side Scatter (SS) dual parameter plot is used to gate main cell population. Fluorescence is collected using three lasers: the 488 nm excitation laser with 780/60 bandpass emission filter, and using the 633 nm excitation laser with 780/60 bandpass emission filters, collecting 10,000 events at flow rate of ~200 events/second. The data is further analyzed using MODFIT LT Flow Cytometry Modeling Software from Verity Software House, Inc. to look at ratio of G2/G1 and the % CV of G1 phase. The data indicated that Compound 19 is an effective stain for use in DNA content cell cycle analysis, as excited by both lasers, and emits in the near-IR region of the spectrum. Typical DNA content cell cycle histograms indicate G0G1 phase, S phase, and G2M phase, as obtained on the live cell gate, with all concentrations of the compound. Further analysis using MODFIT Software shows the compound stains live cells with % CV of G1-phase <8% and exhibits linearity of staining.

Data for live Jurkat cells suspended in RPMI media+10% FBS treated with 20 µM Compound 19 and incubated for 30 minutes at room temperature (using the red 633 nm laser and 780/60 emission) produced a typical cell cycle histogram with % CV of G1-phase is 6.43% and G2/G1 ratio is 1.83, results within the limits of the cell cycle model. Data collection using the blue 488 laser with 780/60 emission also produced a typical cell cycle histogram with % CV of G1-phase is 8.0% and G2/G1 ratio is 1.86.

Example 43

DNA Staining of Live Cells and DNA Content Cell Cycle Analysis Using Flow Cytometry (Compound 20)

Live Jurkat cells suspended in RPMI media+10% FBS were stained with 5 µM, 10 µM, and 20 µM Compound 20 and analyzed with flow cytometry, as described in Example 42. The results show that Compound 20 is an effective stain for use in DNA cell cycle analysis as excited by both lasers and emits in the near-IR region of the spectrum. The cell cycle histogram for the compound, tested at 20 µM concentration, collected using a red 633 nm laser and 780/60 emission, showed G0G1 phase, S phase, and G2M phase and gave a % CV of G1-phase of 6.41% and G2/G1 ratio of 1.84, results within the limits of the cell cycle model.

Example 44

Comparison of DNA Stains on Cell Viability

Live Jurkat cells are suspended at $5 \times 10^5$ cells/ml in complete RPMI media with 10% FBS. Four aliquots of 10 ml each of the cell suspension are made. A final concentration of 5 µM Hoechst 33342 (Invitrogen Corporation) is added to one aliquot, a final concentration of 5 µM DRAQ5 (Biostatus Limited, UK) is added to one aliquot, a final concentration of 5 µM Compound 9 is added to one aliquot, and one aliquot remains untreated as a control. All four aliquots are placed in a 37° C. waterbath for 30 minutes in protected from light. After the incubation, all cell suspensions are centrifuged, the cells are pelleted and the supernatant discarded. To each aliquot, 5 ml media is added. Four culture flasks are prepared by adding 35 ml media to each. One 5 ml aliquot of cells is added to one flask for each on the four cell suspensions aliquots. The flasks are placed in a 37° C. incubator with 5% $CO_2$ in the dark for 72 hours. Each flask of cells is then gently mixed and cell suspension is removed for testing. The cell concentration and image is performed using the Cellometer instrument from Nexcelom. Percentage and absolute cell counts of live and dead cells for each treatment are determined using the LIVE/DEAD Viability/Cytotoxicity Kit (Invitrogen Corporation, Carlsbad, Calif.) with COUNTBRIGHT Absolute Counting Beads (Invitrogen Corporation). This involves adding one ml cell suspension to a 12×75 mm test tube and adding 2 µl of a 50 µM calcein AM solution to identify living cells and 4 µl of a 2 mM ethidium homodimer-1 solution to identify dead cells. The cell suspension is mixed and incubated for 20 minutes at room temperature protected from light. After the end of the incubation, 50 µl of well mixed COUNTBRIGHT absolute counting beads are added to each test tube. Each sample is run through the Becton Dickinson (BD) LSRII Flow Cytometer. Forward Scatter (FS) versus Side Scatter (SS) dual parameter plot is used to gate main cell population, and a separate gate is made around the bead population. Fluorescence is collected using 488 nm excitation laser with 530/30 bandpass and 610/20 bandpass emission filters. Markers on a dual parameter plot of calcein fluorescence versus ethidium homodimer-1 fluorescence is used to obtain percent of cells which are living and dead, as well as number of cell events recorded. By using the COUNTBRIGHT absolute counting beads assay, the absolute number of living and dead cells is calculated by using the equation: $A/B \times C/D$ = concentration of cells/µL (A=number of cell events, B=number of bead events, C=assigned bead count, D=volume of the sample in µl). Table 3 summarizes the results of the experiment. Treatment of cells with the 5 µM DRAQ5 compound killed most of the cells. Treatment with 5 µM Hoechst 33342, a compound known for use with live cell studies, maintained a majority of cells as living. Treatment with 5 µM Compound 9b maintained a majority of cells as living.

TABLE 3

Comparison of Dyes in Cell Viability Assay

| Sample | Cell Count (Cellometer) (cells/mL) | Cell Count (Flow Cytommetry) (cells/mL) | % Living Cells | % Dead Cells |
|---|---|---|---|---|
| Control | $1.26 \times 10^6$ | $3.15 \times 10^5$ | 96.4 | 3.2 |
| Hoechst 33342 | $2.6 \times 10^5$ | $0.9 \times 10^5$ | 57.7 | 39.3 |
| DRAQ-5 | Too few cells to count | $0.08 \times 10^5$ | 2.1 | 95.7 |
| Compound 9 | $2.54 \times 10^5$ | $0.7 \times 10^5$ | 71.2 | 26.4 |

Example 45

Comparison of DNA Stains for Staining Live Cells

Figure 3:
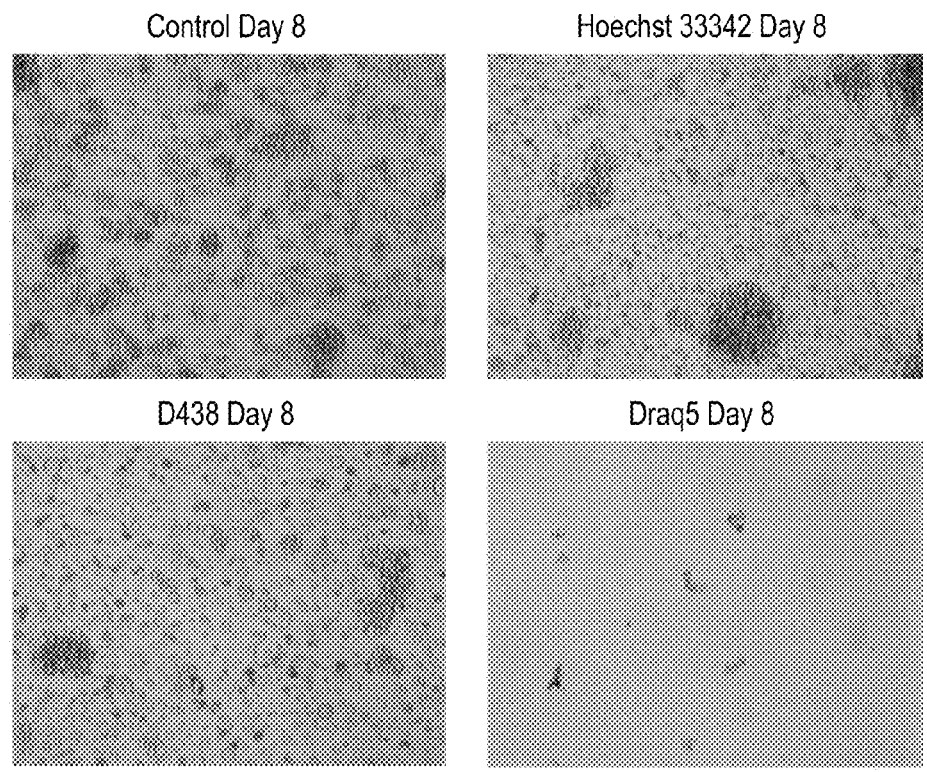
FIG. 3 shows brightfield images for cell cultures taken after 8 days cell growth post sort for each treatment type (Control, Hoechst 33342; DRAQ5; and Compound 9]).

Jurkat cells were suspended at $5 \times 10^5$ cells/ml in complete RPMI media with 10% FBS and stained with either 5 µM Compound 9, 5 µM Hoechst 33342, or 5 µM DRAQ5 for 30 minutes at 37° C. protected from light. A control sample was also prepared with no dye treatment. Cells were washed and resuspended at $1 \times 10^7$ cells/ml in Complete RPMI+10% FBS media for sorting. Approximately 2 million Jurkat cells were sorted for each treatment by gating on the main cell population by scatter using a BD FACS Aria cell sorter. Cells were washed and plated at $1 \times 10^5$ cells/ml in complete media and grown at 37 C with 5% $CO_2$. Cell Viability was assayed using the LIVE/DEAD Viability/Cytotoxicity Kit at 1, 2, and 3 days post sort (as described in Example 44). Brightfield images of cell growth after 8 days cell growth were collected. DRAQ5 exhibited the highest cytotoxicity of all the compounds. Compound 9 and Hoechst 33342 were very similar in post-sort viability, but less than non-stained control cells. The percent of live cells decreased similarly in both Compound 9 and Hoechst 33342 treatments. However, by day 3, Compound 9 and Hoechst 33342 treated cells were beginning to divide again, indicated by the upswing in cell number and concentration of live cells. Visual inspection of the culture showed the characteristic grape clusters of growing Jurkat cells, not seen with DRAQ5-treated cells. Compound 9 produced very similar results to the live cell sorting standard Hoechst 33342, while DRAQ5 treated cells did not grow (FIG. 3).

Example 46

DNA Staining of Live Cells and DNA Content Cell Cycle Analysis Using Flow Cytometry Compound 9 is diluted as a 5 mM concentration in DMSO. Live Jurkat cells are suspended at $5\times10^5$ cells/ml in RPMI media with 10% Fetal Bovine Serum (FBS). Compound 9 was is added to each of one mL cell suspensions at concentrations 2.5 µM, 5 µM, 10 µM and then incubated at 37° C. for 15 minutes while protected from light. Cells are run through the Becton Dickinson (BD) LSRII Flow Cytometer. Forward Scatter (FS) vs Side Scatter (SS) dual parameter plot is used to gate main cell population. Fluorescence is collected using two lasers: the 488 nm excitation laser with 695/40 bandpass emission filter, and using the 633 nm excitation laser with 695/40 bandpass emission filter. Collection of 10,000 events gated on the main population of cells was performed using a flow rate of ~200 events/second. The dye demonstrated staining for DNA content cell cycle as excited by both lasers and having emission in the near-IR region of the spectrum. A typical DNA cell cycle histogram was generated, showing G0/G1 phase, S phase, and G2/M phase, as obtained on the live cell gate, with all concentrations of the compound.

Example 47

DNA Staining of Live Cells and DNA Content Cell Cycle Analysis Using Flow Cytometry Live Jurkat cells are suspended at $5\times10^5$ cells/ml in RPMI media Compound 9 is added to each of one mL cell suspensions at final concentrations 1.25 µM, 2.5 µM, 5 µM, and 10 µM and then incubated at 37° C. and room temperature for 15 minutes while protected from light. Cells are run through the Becton Dickinson (BD) LSRII Flow Cytometer. Forward Scatter (FS) versus Side Scatter (SS) dual parameter plot is used to gate main cell population. Fluorescence is collected using two lasers: the 488 nm excitation laser with 695/40 bandpass emission filter, and using the 633 nm excitation laser with 695/40 bandpass emission filters, collecting 10,000 events at flow rate of ~200 events/second. The data is further analyzed using MODFIT LT Flow Cytometry Modeling Software from Verity Software House, Inc. to look at ratio of G2/G1 and the % CV of G1 phase. Compound 9 was shown to be an effective stain for use in DNA content cell cycle analysis and is excited by both lasers with emission in the near-IR region of the spectrum. Typical DNA cell cycle histogram are demonstrated showing G0G1 phase, S phase, and G2M phase, as obtained on the live cell gate, with all concentrations of the compound tested. Further analysis using MODFIT Software shows the compound stains live cells for DNA cell cycle where the % CV of G1-phase <8%, and the observed ratio indicates linearity of staining.

Example 48

Imaging of Cells Stained with Near-IR DNA Stain

Figure 4:
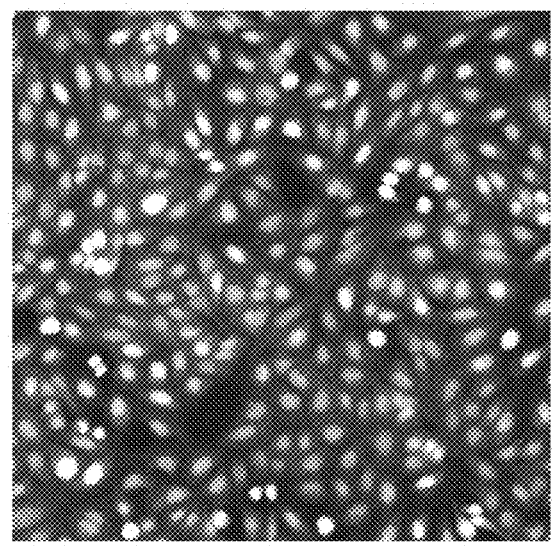
FIG. 4 shows an image of U-2 OS cells (ATCC HTB-96) with simultaneous fixation and labeling with 3.7% formaldehyde and 20 μM Compound 9 for 30 minutes at room temperature.
Figure 5:
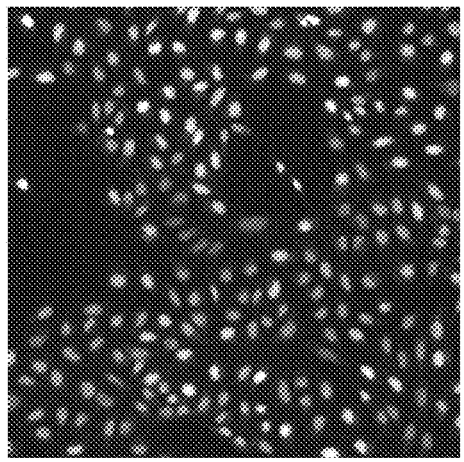
FIG. 5 shows an image of U-2 OS cells (ATCC HTB-96) with 20 μM Compound 9 for 30 minutes at 37° C.
Figure 6:
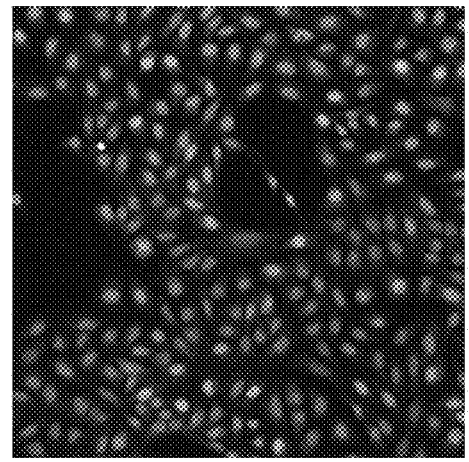
FIG. 6 shows an image of the field of cells from FIG. 5 after fixation with 3.7% formaldehyde.
Figure 7:
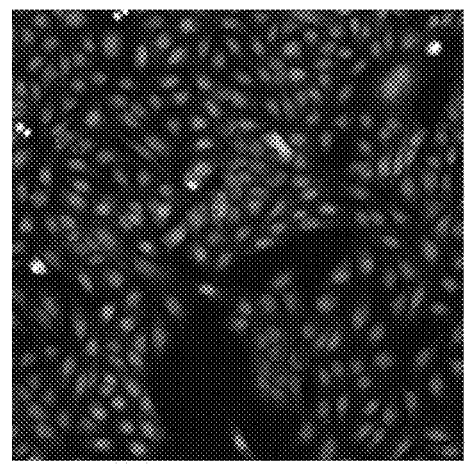
FIG. 7 shows an image of U-2 OS cells (ATCC HTB-96) fixed with 3.7% formaldehyde for 30 minutes at room temperature and then labeled with 20 μM Compound 9 for 30 minutes at room temperature.

Live U-2 OS cells (ATCC HTB-96) were treated with Compound 9 under various conditions and imaged with a 10×/0.3 objective on an ArrayScan VTI automated microscope platform (ThermoFisher/Cellomics). Using various combinations of sample preparation and labeling conditions, the tested compound produced prominent nuclear and relatively dim cytsolic staining. Such staining patterns have been routinely utilized in auto-focus and cell identification in automated microscopy. Cells were fixed with 3.7% formaldehyde (diluted from Sigma F1635) in the presence of 20 µM Compound 9 for 30 minutes at room temperature. The fixed cells were imaged and show similar prominent nuclear and dim cytosolic labeling (FIG. 4). The results indicate that labeling with this compound may be performed simultaneously with fixation. The same staining pattern for cells stained with 20 µM Compound 9 for 30 minutes at 37° C. and imaged live is shown in FIG. 5. Cells of the same field as shown in FIG. 5, after staining with Compound 9, were fixed with 3.7% formaldehyde for 30 minutes at room temperature and imaged (FIG. 6). The results indicate that fixability of the labeling produced in live cells. FIG. 7 shows a staining pattern for cells fixed with 3.7% formaldehyde for 30 min. at room temperature and then stained with 20 µM Compound 9 for 30 min at room temperature.

Example 49

Cytotoxicity Study Adherent Cell Analysis Via HCS

HeLa and U2OS cells were stained with DRAQ5, Hoechst 33342, mitoxantrone, and Compound 9 over a range of concentrations to evaluate the effect of the tested DNA stains on cell proliferation over time. HeLa and U2OS cells were plated at 3000 cells/well and allowed to recover overnight before proceeding with dye incubations. Cells were incubated with 0, 1, 5 or 10 µM Compound 9, Hoechst 33342, mitoxantrone, and DRAQ5 for 30 minutes at culture conditions in DPBS with glucose, washed and then placed back into media at culture conditions. Plates were stained with 100 nM YOYO-1 (Invitrogen Corporation) before being fixed and stained with 1:1000 Hoechst 33342 (total cell number) at 24, 48 and 72 hours post dye incubation. Cells were imaged with the ArrayScan VTI immediately following staining and fixation. Data obtained were from repetitions of 4 wells/condition with 10 images taken per well.

Figure 8:
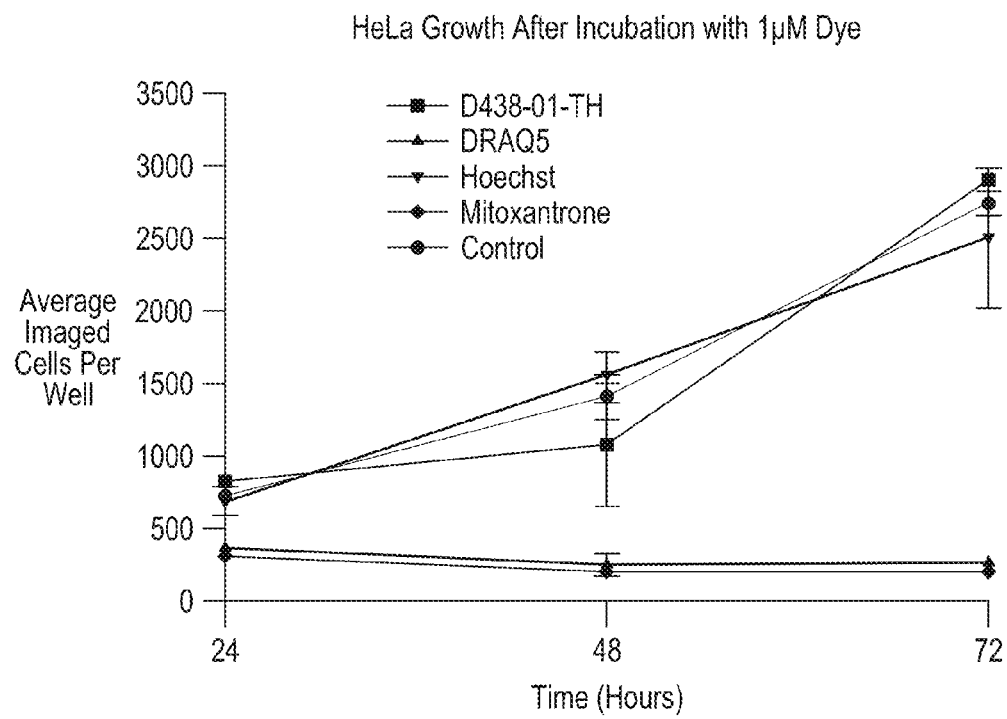
FIG. 8 is a plot showing HeLa cell growth after incubation with various DNA stains (1 μM).
Figure 9:
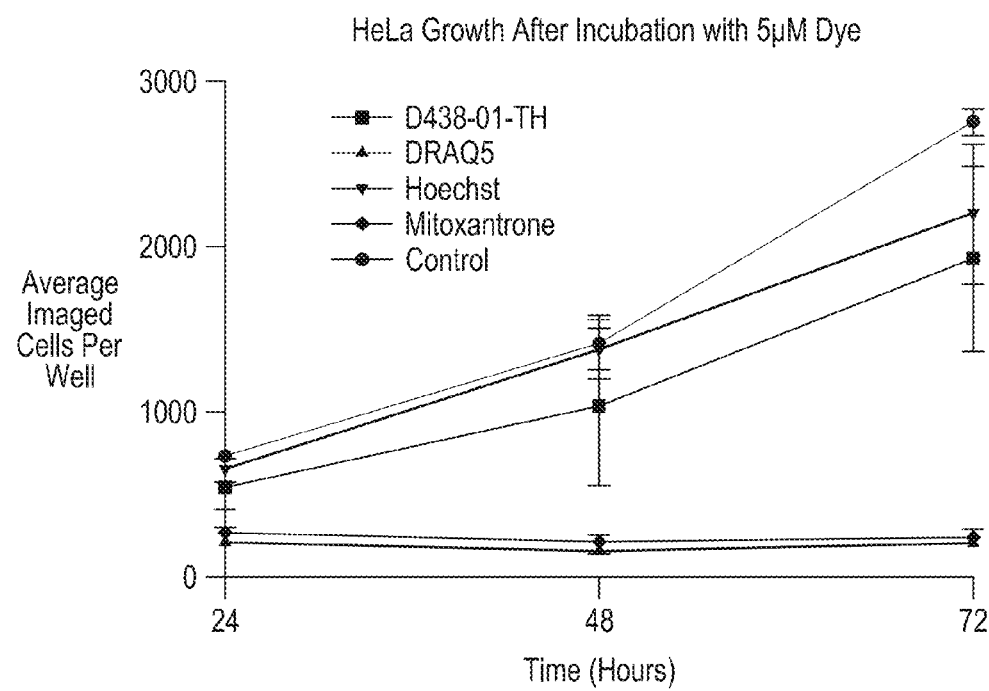
FIG. 9 is a plot showing HeLa cell growth after incubation with various DNA stains (5 μM).
Figure 10:
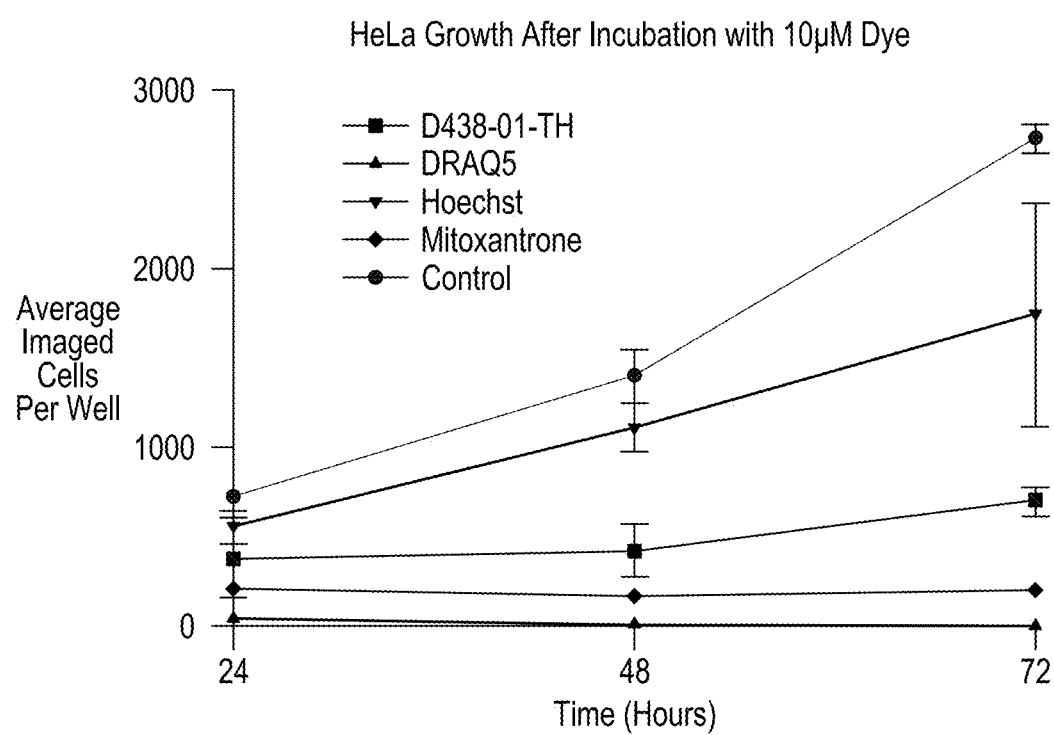
FIG. 10 is a plot showing HeLa cell growth after incubation with various DNA stains (10 μM).
Figure 11:
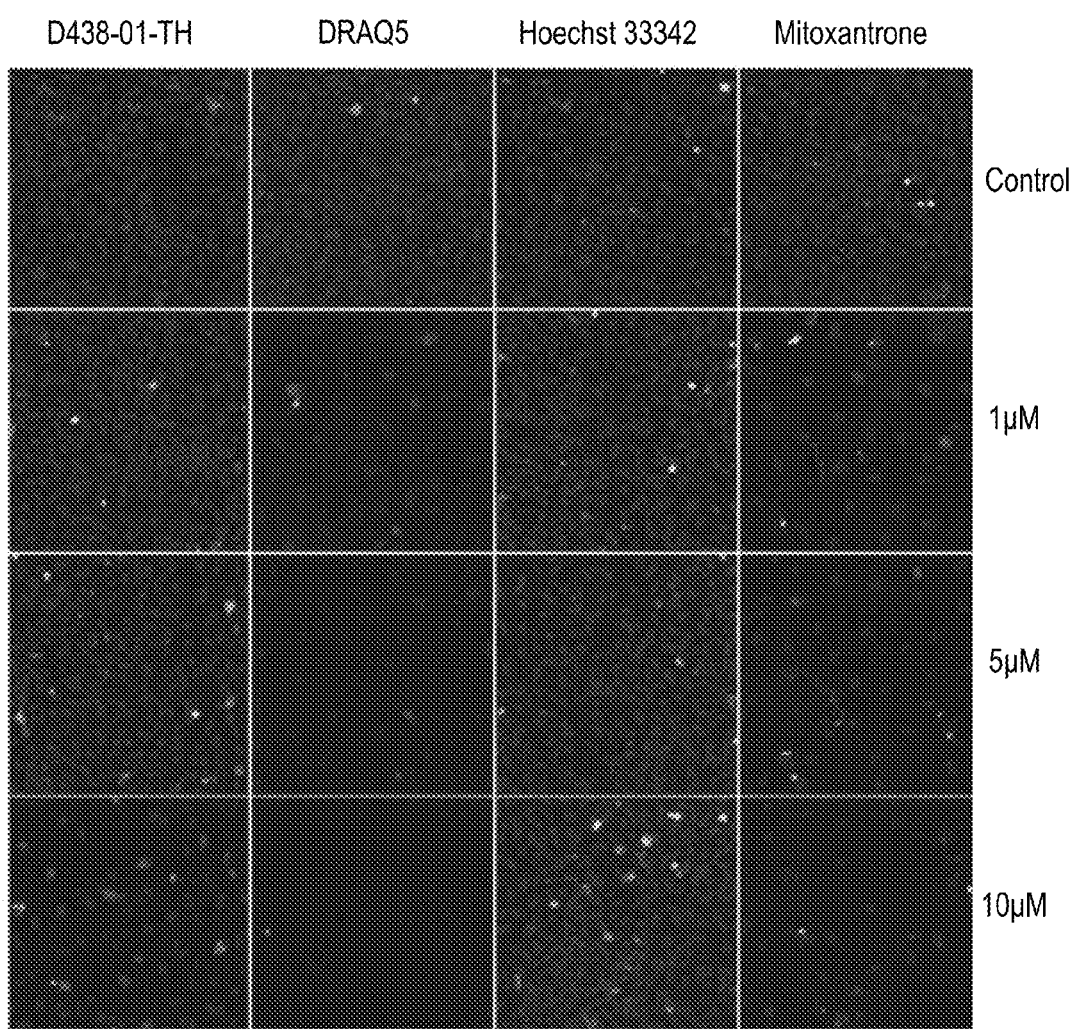
FIG. 11 is an image summary of HeLa cells 72 hours post dye incubation for various DNA stains.

At all concentrations tested, cells stained with DRAQ5 showed no proliferation as compared to control cells and at high concentrations (5 µM or more) high membrane permeability (indicated by YOYO-1) in those cells still adhered to the plate. Plots showing HeLa cell growth after incubation with the DNA stains at concentrations of 1, 5, and 10 µM are shown in FIGS. 8-10. Cells stained with low concentrations of Compound 9 (5 µM or less) showed proliferation rates comparable to Hoechst 33342 stained and control cells. At higher concentration (10 µM), Compound 9 stained cells showed diminished proliferation, but the cells left adhered to the plate appeared to have intact membranes. FIG. 11 shows the image summary of HeLa cells 72 hours post dye incubation for the DNA stains tested.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of staining a biological sample containing nucleic acid, comprising:
 a) contacting the biological sample with a compound having the structure:

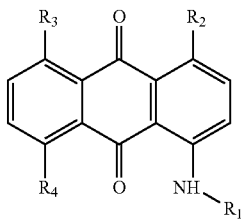

wherein $R_2$, $R_3$, and $R_4$ are independently OH or $NHR_9$, wherein $R_9$ is H or $(CH_2)_nCOR_5$ and $R_1$ is $-(CH_2)_nCOR_5$, wherein $R_5$ is $NH(CH_2)_mNR_7R_8$ or $NH(CH_2)_mN^+R_7R_8R_{10}$, wherein $R_7$, $R_8$ and $R_{10}$ are independently H or $C_{1-10}$ alkyl, m is 2 to 10, and n is 1 to 5 to form a mixture;
 b) incubating the mixture for a sufficient amount of time for the compound to associate with nucleic acid in the sample to form an incubated sample;
 c) exciting the incubated sample by illumination with light of an appropriate wavelength to generate a detectable optical response; and
 d) detecting the optical response of the compound.

2. The method of claim 1 wherein the biological sample comprises cells.

3. The method of claim 2 wherein the cells are treated with a cell fixative reagent, or a cell fixative reagent combined with a cell permeabilizing reagent, or a cell permeabilizing reagent.

4. The method of claim 1 wherein the biological sample comprises fixed cells, or fixed and permeabilized cells, fixed and permeabilized cells, or free cell nuclei.

5. The method of claim 1 wherein the biological sample comprises live cells.

6. The method of claim 1, wherein said compound is in solution.

* * * * *